United States Patent
Kovach et al.

(10) Patent No.: US 8,376,943 B2
(45) Date of Patent: Feb. 19, 2013

(54) PATIENT EVENT INFORMATION

(75) Inventors: Peter J. Kovach, Fridley, MN (US); Warren W. Ball, Coon Rapids, MN (US); Sarah B. Alme, Blaine, MN (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 713 days.

(21) Appl. No.: 12/236,211

(22) Filed: Sep. 23, 2008

(65) Prior Publication Data

US 2009/0082640 A1 Mar. 26, 2009

Related U.S. Application Data

(60) Provisional application No. 60/974,726, filed on Sep. 24, 2007.

(51) Int. Cl.
*A61B 5/00* (2006.01)

(52) U.S. Cl. ............... 600/300; 607/2; 607/45; 607/46; 607/59; 607/60

(58) Field of Classification Search .................. None
See application file for complete search history.

(56) References Cited

U.S. PATENT DOCUMENTS

| | | | | |
|---|---|---|---|---|
| 5,518,001 | A * | 5/1996 | Snell ............................ | 600/510 |
| 6,155,267 | A | 12/2000 | Nelson | |
| 6,540,674 | B2 * | 4/2003 | Zadrozny et al. ............ | 600/300 |
| 6,990,372 | B2 * | 1/2006 | Perron et al. .................. | 600/544 |
| 7,006,872 | B2 | 2/2006 | Gielen et al. | |
| 7,280,867 | B2 | 10/2007 | Frei et al. | |
| 2001/0039504 | A1 | 11/2001 | Linberg et al. | |
| 2002/0120187 | A1 | 8/2002 | Eiffert et al. | |
| 2003/0078621 | A1 | 4/2003 | Ujhelyi et al. | |
| 2003/0177031 | A1 | 9/2003 | Malek | |
| 2004/0133119 | A1 | 7/2004 | Osorio et al. | |
| 2004/0158119 | A1 | 8/2004 | Osorio et al. | |
| 2005/0060007 | A1 | 3/2005 | Goetz | |
| 2005/0113703 | A1 * | 5/2005 | Farringdon et al. ........... | 600/509 |
| 2005/0240244 | A1 | 10/2005 | Leinders et al. | |
| 2006/0020225 | A1 | 1/2006 | Gerber et al. | |
| 2006/0094972 | A1 | 5/2006 | Drew | |
| 2006/0235489 | A1 * | 10/2006 | Drew et al. ..................... | 607/60 |
| 2007/0040692 | A1 | 2/2007 | Smith et al. | |
| 2007/0123786 | A1 | 5/2007 | Grandjean et al. | |
| 2007/0213783 | A1 * | 9/2007 | Pless ............................... | 607/42 |
| 2007/0252714 | A1 | 11/2007 | Rondoni et al. | |
| 2007/0255346 | A1 * | 11/2007 | Rondoni et al. ................ | 607/59 |
| 2007/0265664 | A1 * | 11/2007 | Gerber et al. ..................... | 607/2 |
| 2007/0265681 | A1 * | 11/2007 | Gerber et al. .................... | 607/46 |
| 2008/0058664 | A1 * | 3/2008 | Mirro ............................. | 600/523 |

(Continued)

OTHER PUBLICATIONS

U.S. Appl. No. 12/236,260, filed Sep. 23, 2008, entitled "Therapy Adjustment Based on Patient Event Indication," by Giftakis et al.

(Continued)

*Primary Examiner* — Sam Yao
*Assistant Examiner* — Davin K Sands
(74) *Attorney, Agent, or Firm* — Shumaker & Sieffert, PA

(57) ABSTRACT

Patient input indicating the occurrence of an event and information relating to the event may be collected by a computing device. In some examples, the patient input is received via an event indication input mechanism of a medical device programmer. A clinician may review the event information to evaluate the efficacy of a therapy system (e.g., a particular therapy program or program group) or a patient's condition. In one example, a patient may activate an event indication input mechanism to indicate the occurrence of a seizure symptom, and input information relating to the seizure, such as the duration, severity, type of seizure or efficacy of a therapy system implemented to manage seizures.

32 Claims, 23 Drawing Sheets

U.S. PATENT DOCUMENTS

| | | |
|---|---|---|
| 2008/0269812 A1 | 10/2008 | Gerber et al. |
| 2008/0270188 A1 | 10/2008 | Garg et al. |
| 2008/0300649 A1 | 12/2008 | Gerber et al. |
| 2010/0256592 A1 | 10/2010 | Gerber et al. |

OTHER PUBLICATIONS

U.S. Appl. No. 12/236,316, filed Sep. 23, 2008, entitled "Patient Event Information," by Giftakis et al.

U.S. Appl. No. 60/974,726, filed Sep. 24, 2007, entitled "Therapy Adjustment" by Kovach et al.

U.S. Appl. No. 60/974,691, filed Sep. 24, 2007, entitled "Therapy Adjustment" by Giftakis et al.

Office Action dated Oct. 11, 2011 for U.S. Appl. No. 12/236,260, (10 pgs.).

Response dated Jan. 11, 2012 for U.S. Appl. No. 12/236,260, (5 pgs.).

Office Action dated Aug. 8, 2011 for U.S. Appl. No. 12/236,316, (25 pgs.).

Responsive Amendment dated Nov. 8, 2011 for U.S. Appl. No. 12/236,316, (17 pgs.).

Office Action from U.S. Appl. No. 12/236,316, dated Oct. 9, 2012, 29 pp.

* cited by examiner

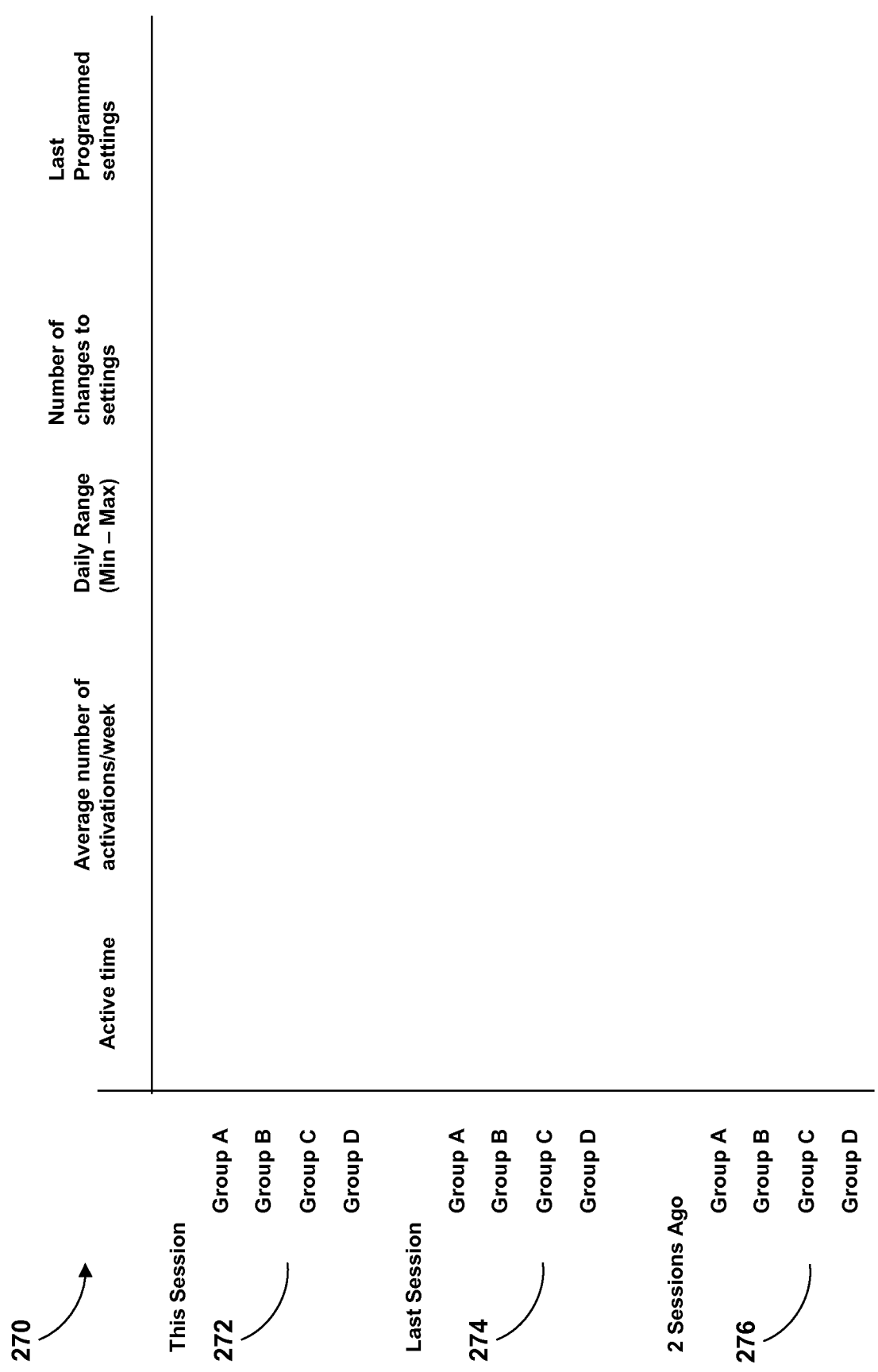

| THIS SESSION | | PRIOR SESSION | |
|---|---|---|---|
| Session | 12-May-2007 to 5-July-2007 | Session | 4-February-2007 to 12-May-2007 |
| Events | Stim Reset By User | Events | Stim Reset By User |
| Total | 48 | Total | 36 |
| Avg. Per Day (Type1) | .48 Avg Per Day | Avg. Per Day (Type1) | .36 Avg Per Day |
| Avg. Per Day (Type2) | .48 Avg Per Day | Avg. Per Day (Type2) | .36 Avg Per Day |
| Avg. Per Day (Type3) | .48 Avg Per Day | Avg. Per Day (Type3) | .36 Avg Per Day |
| Avg Per Month (Type1) | 15 Avg Per Month | Avg Per Month (Type1) | 10 Avg Per Month |
| Avg Per Month (Type2) | 15 Avg Per Month | Avg Per Month (Type2) | 10 Avg Per Month |
| Avg Per Month (Type3) | 15 Avg Per Month | Avg Per Month (Type3) | 10 Avg Per Mont |

Type1 = Grand Tonic Clonic
Type2 = Complex Partial
Type3 = Simple Partial

Type1 = Grand Tonic Clonic
Type2 = Complex Partial
Type3 = Simple Partial

Therapy
Current Medications (Daily) CBZ (900 mg)

Therapy
Current Medications (Daily) CBZ (900 mg)

INSS Diagnostics
Battery Status    ERI 7.8 years

INSS Diagnostics
Battery Status    ERI 8.0 years

| | | Program | Ohms | mA | | | Program | Ohms | mA |
|---|---|---|---|---|---|---|---|---|---|
| Lead Impedance | L STN | 327 | 11.235 | | Lead Impedance | L STN | 305 | 10.155 | |
| | R STN | 368 | 10.075 | | | R STN | 329 | 10.095 | |

FIG. 9F

PATIENT EVENT INFORMATION

This application claims the benefit of U.S. Provisional No. 60/974,726 to Kovach et al., entitled, "PATIENT EVENT INFORMATION" and filed on Sep. 24, 2007, which is incorporated herein by reference in its entirety.

TECHNICAL FIELD

The disclosure relates to information visualization, and more particularly, collecting and displaying information related to a therapy delivery.

BACKGROUND

Medical devices may be used to deliver therapy to patients to treat a variety of symptoms or conditions, such as epilepsy, chronic pain, tremor, Parkinson's disease, psychiatric disorders, neuralgia, urinary or fecal incontinence, sexual dysfunction, obesity, or gastroparesis. A medical device may deliver stimulation therapy via leads that include electrodes located proximate to the spinal cord, pelvic nerves, stomach, or within the brain of a patient. The stimulation site may be selected on the particular patient condition being managed by the stimulation system. In some cases, at least some electrodes may be integrated with an implantable pulse generator.

In another type of therapy, a medical device may deliver a drug or another therapeutic agent to a specific tissue site within the patient via a catheter attached to the medical device. In any case, the medical device is used to provide treatment to the patient as needed in order in increase the quality of life of the patient, such as to manage a patient condition. The medical device may be implanted or located externally, depending upon the type of therapy and needs of the patient.

A clinician may program the medical device to effectively treat the patient. For example, the clinician may define the therapy to be delivered to a patient by selecting values for one or more programmable therapy parameters. The therapy parameters may define a therapy program, and in some cases, a medical device delivers therapy in accordance with more than one program, which may be arranged in a program group. As one example, in the case of electrical stimulation, the clinician may select an amplitude, which may be a current or voltage amplitude, and a pulse width for a stimulation waveform to be delivered to the patient, as well as a rate at which the pulses are to be delivered to the patient. Programmable therapy parameters also may include electrode combinations and polarities. The clinician may also create multiple programs having various different therapy parameter combinations that the patient may use as desired in order to find the most effective therapy parameters to treat a condition.

SUMMARY

In general, the disclosure is directed to obtaining information relating to a patient event upon receiving an indication that the patient event occurred. The event may be, for example, the occurrence of a symptom related to the patient's condition, such as an aura related to a seizure or a headache related to chronic migraines. In some examples, the indication that a patient event occurred is received via an external programmer that includes an event indication button. The button is not limited to depressible buttons, but may also be presented as a selectable portion of a touch screen, a knob, or any other suitable mechanisms or media of receiving patient input. For convenience, any such media and event indication interfaces may be generally referred to herein as a button or an input mechanism.

A processor of the programmer or another computing device may generate an event marker upon activation of the event indication button by the patient. For example, if the patient detects an aura, the patient may activate the event indication button, and, in response, the processor may generate an event marker. The patient may provide information relating to the patient event (i.e., "event information"). For example, in examples in which the condition of the patient is epilepsy, the event information may include the type of seizure, severity of seizure, duration of seizure, drug type and dose, a subjective rating of the efficacy of therapy that is delivered to manage the patient's seizure disorder, and the like. The programmer may provide a user interface that is configured to receive the event information from the patient, and, in some examples, may prompt the patient for the information.

In some examples, the programmer may also record physiological parameter values, such as, but not limited to, an electroencephalogram (EEG) signal, electrocardiogram (ECG) signal, respiratory signal, blood pressure or body temperature, which may be monitored by a therapy delivery device or a separate implanted or external sensing device. The event information may be associated with an event marker and stored in a memory of the programmer, an implantable medical device, or another computing device for later retrieval and analysis by a clinician.

A clinician may review the event information to evaluate the patient's condition, as well as evaluate a therapy system that may be implemented to manage the patient's condition. In some examples, a computing device, such as a clinician programmer, may present the event information in any one or more of display formats, such as lists, tables, bar graphs, histograms, line graphs, Venn diagrams, pie charts or other graphical or linear display formats. Displaying the event information in one or more of these formats may assist a clinician in understanding the individual events and the progression of events over the course of time. In some examples, displaying the event information in one or more of these formats may assist a clinician in determining the efficacy of a therapy program and in determining whether any changes to the therapy program are desired or necessary. The event information may be presented in a meaningful format that enables the clinician to more quickly review and ascertain relevant data records, relationships between the different data records or trends in the data.

In one aspect, the disclosure is directed to a method comprising receiving an indication of a patient event, where the event is related to a condition of a patient, automatically generating an event marker, receiving event information relating to the patient event from the patient, wherein the event information indicates an efficacy of therapy that is delivered to the patient to manage the condition, associating the event information with the event marker, and storing the event information within a memory.

In another aspect, the disclosure is directed to a system comprising an event indication input mechanism, a user interface, a memory, and a processor that generates an event marker upon activation of the event indication input mechanism and receives event information relating to a patient condition from a patient via the user interface. The processor associates the event marker with the event information and stores the event information and event marker in the memory. The event information comprises an efficacy of therapy that is delivered to the patient to manage the patient condition.

In another aspect, the disclosure is directed to a method comprising receiving seizure event information, wherein the seizure event information comprises an efficacy of therapy system implemented to manage the seizure, and wherein the seizure event information is associated with an event marker, and generating a display of the seizure event information and the event marker.

In another aspect, the disclosure is directed to a system comprising an event indication input mechanism that receives an indication of a patient event from a patient, a processor that generates an event marker in response to the indication of the patient event, a user input mechanism that receives event information relating to the patient event from the patient, wherein the event information comprises an efficacy of a therapy system implemented to manage a seizure, and a memory that stores the event marker and the event information In another aspect, the disclosure is directed to a computer-readable medium comprising (or storing) instructions. The instructions cause a programmable processor to receive an indication of a patient event, where the event is related to a condition of a patient, generate an event marker, receive event information relating to the patient event from the patient, where the event information indicates an efficacy of therapy that is delivered to the patient to manage the condition, associate the event information with the event marker, and store the event information within a memory.

In another aspect, the disclosure is directed to a computer-readable medium comprising instructions. The instructions cause a programmable processor to receive seizure event information, wherein the seizure event information comprises an efficacy of a therapy system implemented to manage a seizure, and wherein the seizure event information is associated with an event marker, and generate a display of the seizure event information and the event marker.

In another aspect, the disclosure is directed to a system comprising means for receiving an event indication from a patient, means for generating an event marker in response to the event indication, means for receiving event information relating to a patient event from the patient, and means for storing the event marker and the event information. The event information indicates an efficacy of therapy that is delivered to the patient to manage the condition.

In another example, the disclosure is directed to a system comprising means for receiving an event indication from a patient, means for generating an event marker in response to the event indication, means for receiving event information relating to a patient event from the patient, where the event information comprises an efficacy of a therapy system implemented to manage a seizure, and means for storing the even marker and the event information.

In another aspect, the disclosure is directed to a computer-readable medium comprising instructions. The instructions cause a programmable processor to perform any part of the techniques described herein.

The details of one or more examples of the disclosure are set forth in the accompanying drawings and the description below. Other features, objects, and advantages of the systems and methods described herein will be apparent from the description and drawings, and from the claims.

BRIEF DESCRIPTION OF THE DRAWINGS

FIGS. 8A-8H illustrate example user interfaces that may be presented by a computing device, such as a programmer or a workstation.

FIGS. 9A-9F illustrate example displays for presenting event information.

DETAILED DESCRIPTION

Figure 1:
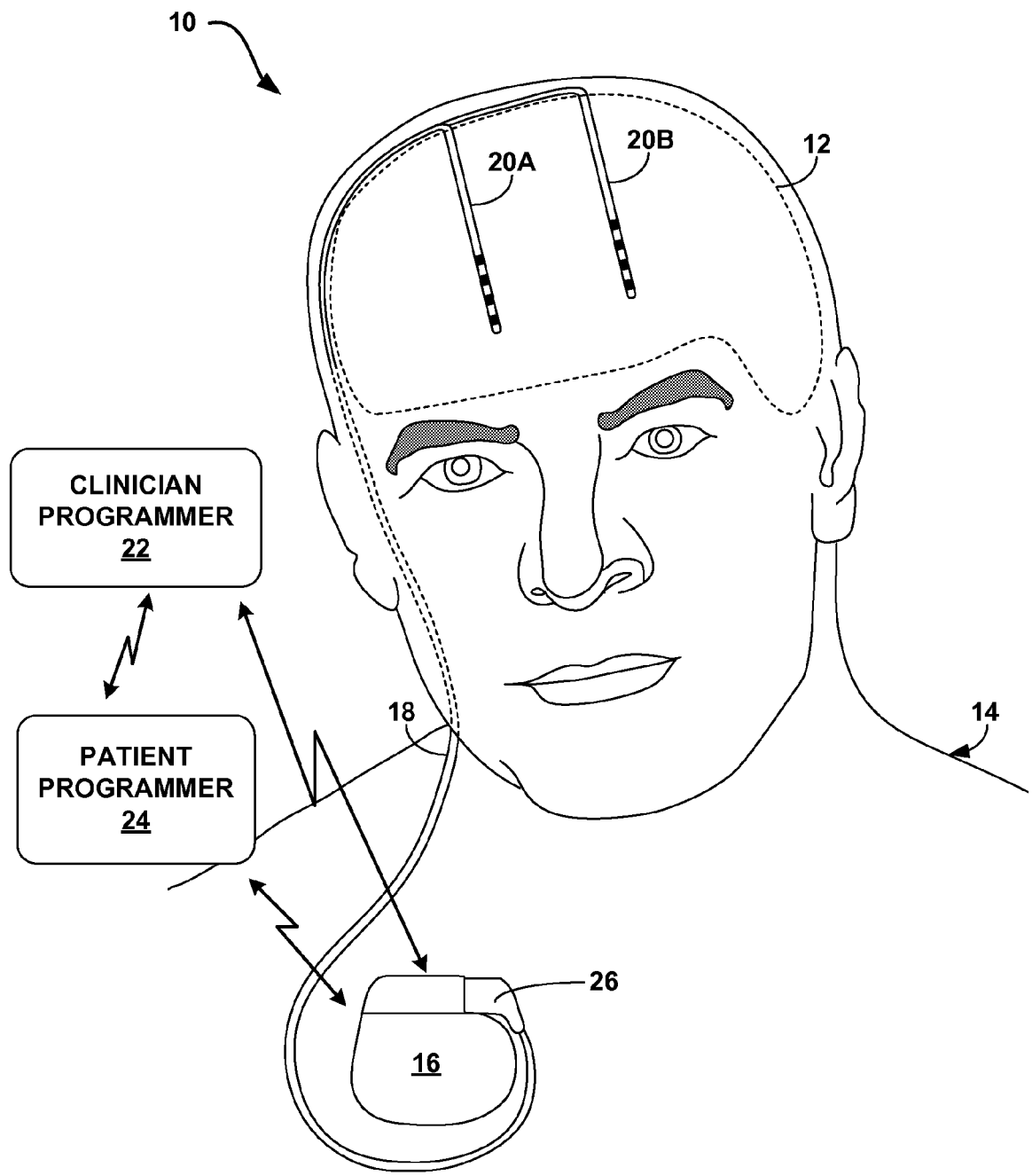
FIG. 1 is a conceptual diagram illustrating an example therapy system that includes an implantable medical device, a patient programmer, and a clinician programmer.

Systems and techniques described herein are useful for evaluating information relating to a patient's condition. The systems and techniques described herein primarily refer to examples in which the patient condition includes seizures. However, in other examples, the systems and methods described herein may be useful in evaluating information related to other patient conditions, such as, for example, patient conditions addressed by therapy systems that include an electrical stimulator, fluid (e.g., therapeutic agent) delivery device or other therapy device that provides pain mitigation, peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles) for mitigation of other peripheral and localized pain (e.g., leg pain or back pain) or sacral nerve stimulation to influence the behavior of the relevant structures, such as the bladder, sphincter and pelvic floor muscles. In addition, the systems and methods described herein may be useful in evaluating information related to other patient conditions such as movement disorders, neurological disorders, psychiatric disorders (e.g., depression, mania, obsessive-compulsive disorder, and the like), and the like. For example, the systems and methods described herein may also be useful with spinal cord stimulation, gastric stimulation, pelvic floor stimulation, peripheral nerve stimulation, peripheral nerve field stimulation, deep brain stimulation and so forth.

Epilepsy is a neurological disorder characterized by the occurrence of seizures, although seizures may also occur in persons who do not have epilepsy. Seizures are typically attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause damage to the brain, which may result in progressive loss of brain function over time.

Therapy delivery systems may be used to treat seizures to mitigate the effects of many patient conditions or disorders. Electrical stimulation therapy or delivery of a fluid (e.g., a drug or another pharmaceutical agent) to the patient may shorten the duration of the seizure, prevent the onset of seizures or minimize the severity of the seizure. In some cases, the electrical stimulation is provided to one or more regions of the brain at regular intervals, substantially continuously or upon the detection or prediction of some event, such as the detection of a seizure by EEG sensors implanted within the brain, or at the direction of the patient or clinician. In the case of drug (or therapeutic agent) delivery therapy, drugs may be orally introduced into the patient or infused directly into a blood stream or one or more regions of the brain of the patient at regular intervals, substantially continuously or upon the detection or prediction of some event, such as the detection of a seizure by EEG sensors implanted within the brain, or at the direction of the patient or clinician.

In open-loop therapy systems, therapy is delivered substantially continuously or at regular intervals for an indefinite period of time without relying on feedback from the system. In contrast, closed-loop or responsive therapy systems deliver therapy in response to the detection or prediction of some event, which may be detected or predicted by monitoring physiological parameters of the patient. In the case of seizures, for example, the closed-loop or responsive therapy system may deliver therapy in response to the detection of a seizure by EEG sensors within the patient's brain or motion detectors that detect the physical symptoms of a seizure. In a closed-loop therapy system, the medical device may continue delivering therapy until it determines the seizure has ceased.

FIG. 1 is a conceptual diagram illustrating an example therapy system 10 that is implanted proximate to brain 12 of patient 14 in order to help manage the patient's seizure disorder. While patient 14 is generally referred to as a human patient, other mammalian or non-mammalian patients are also contemplated. In the example shown in FIG. 1, therapy system 10 may be a deep brain stimulation (DBS) system because therapy system 10 provides therapy directly to deep brain sites, such as sites under the dura mater surrounding brain 12. However, therapy system 10 may also deliver therapy to a surface of brain 12. Therapy system 10 includes implantable medical device (IMD) 16, lead extension 18, leads 20A and 20B, clinician programmer 22, and patient programmer 24. IMD 16 includes a therapy module that delivers electrical stimulation therapy to one or more regions of brain 12 via leads 20A and 20B at regular intervals.

In some examples, stimulation sessions ("on-cycles") are separated by sessions in which no stimulation is delivered ("off-cycles"). Together, the on-cycle and off-cycle define a therapy cycle, which may include more than one on-cycle and/or more than one off-cycle. As one example of a therapy cycle, IMD 16 may deliver stimulation in five minute intervals, where stimulation is delivered for about one minute. That is, in one example therapy cycle, the on-cycle may be about one minute and the off-cycle may be about five minutes. However, other therapy cycles may also be programmed by a clinician. The therapy cycle may depend upon the patient's condition, such as the type of seizures experienced by patient 14, the duration of the seizures or the severity of the seizures, and, in some cases, the therapy delivery site within the patient. In other examples, such as when therapy is delivered substantially continuously, the therapy cycle does not include an off-cycle.

In the example shown in FIG. 1, IMD 16 is implanted within a chest cavity of patient 14. In other examples, IMD 16 may be implanted within other regions of patient 14, such as a subcutaneous pocket in the abdomen of patient 14 or proximate the cranium of patient 14. Implanted lead extension 18 is coupled to IMD 16 via connector block 26, which may include, for example, electrical contacts that electrically couple to respective electrical contacts on lead extension 18. The electrical contacts electrically couple the electrodes carried by leads 20A and 20B (collectively "leads 20") to a therapy module within IMD 16. Lead extension 18 traverses from the implant site of IMD 16 within a chest cavity of patient 14, along the neck of patient 14 and through the cranium of patient 14 to access brain 12. In the example shown in FIG. 1, leads 20 are implanted within the right and left hemispheres, respectively, of brain 12 in order deliver electrical stimulation to one or more regions of brain 12, which may be selected based on many factors, such as the type of seizures patient 14 afflicting patient 14. Neurological disorders that cause seizures, such as epilepsy, may be generated in one or more of regions of the brain, which may differ between patients.

Although leads 20 are shown in FIG. 1 as being coupled to a common lead extension 18, in other examples, leads 20 may be coupled to IMD 16 via separate lead extensions or directly coupled to IMD 16 without the aid of a lead extension. Leads 20 may deliver electrical stimulation to treat any number of neurological disorders or diseases in addition to seizures, such as movement disorders, pain (including acute and chronic pain) or psychiatric disorders. Examples of movement disorders include a reduction in muscle control, motion impairment or other movement problems, such as tremors, rigidity, bradykinesia, rhythmic hyperkinesia, nonrhythmic hyperkinesia, dystonia, and akinesia. Examples of psychiatric disorders may include, for example, major depressive disorder (MDD), bipolar disorder, anxiety disorders, post-traumatic stress disorder, dysthymic disorder, and obsessive-compulsive disorder (OCD).

Leads 20 may be implanted within a desired location of brain 12 via any suitable technique, such as through respective burr holes in a skull of patient 14 or through a common burr hole in the cranium. Leads 20 may be placed at any location within brain 12 such that the electrodes of the leads are capable of providing electrical stimulation to targeted tissue during treatment. Electrical stimulation generated from the signal generator (not shown) within the therapy module of IMD 16 may help prevent the onset of seizures or minimize the severity of seizures. The exact parameter values of the stimulation therapy, such as the amplitude or magnitude of the stimulation signals, the duration of each stimulus, the waveform of the stimuli (e.g., rectangular, sinusoidal or ramped signals), the frequency of the stimuli, and the like, may be specific for the particular target stimulation site (e.g., the region of brain 12) involved as well as the particular patient.

In the case of stimulation pulses, the stimulation therapy may be characterized by selected pulse parameters, such as pulse amplitude, pulse rate, and pulse width. In addition, if different electrodes are available for delivery of stimulation, the therapy may be further characterized by different electrode combinations, i.e., the electrodes of leads 20 that are selected to deliver therapy to patient 14 and the polarity of the selected electrodes. Known techniques for determining the optimal stimulation parameter value may be employed. In one example, electrodes of leads 20 are positioned to deliver stimulation therapy to an anterior nucleus of the thalamus of brain 12 of patient 14, and stimulation therapy is delivered via a select combination of the electrodes to the anterior nucleus of the thalamus with electrical stimulation including a frequency of 145 hertz (Hz), a voltage of about 4 volts to about 5 volts, and a pulse width of about 90 microseconds. However, other examples may implement stimulation therapy including other stimulation parameter values.

Other stimulation targets for epilepsy may include, but are not limited to, the caudate nucleus, locus coeruleus, cerebellum, subthalamic nucleus, cingulate, substantia nigra, and thalamic structures such as the centromedian nucleus, centrolateral nucleus, and dorsomedial nucleus of brain 12. Stimulation may also be directed in a brain lobe, such as the frontal, temporal, parietal and occipital lobes. In some examples, if patient 12 suffers frontal lobe seizures, stimulation electrodes of leads 20 may be positioned directly in the premotor cortex, the motor cortex, and in neural pathways connecting them. In other examples, if patient 12 suffers from seizures that originate in medial temporal lobe (MTL) structures, stimulation may be directed at the hippocampus, amygdala, or in both of these structures. For focal seizures, the stimulation lead may be placed at the site of seizure origin, at or near the seizure focus, as identified with seizure onset localization techniques, including EEG monitoring and brain imaging.

The electrodes of leads 20 are shown as ring electrodes. Ring electrodes may be relatively easy to program and are typically capable of delivering an electrical field to tissue surrounding leads 20. In other examples, the electrodes of leads 20 may have different configurations. For example, the electrodes of leads 20 may have a complex electrode array geometry that is capable of producing shaped electrical fields. The complex electrode array geometry may include multiple electrodes (e.g., partial ring or segmented electrodes) around the perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 14.

In some examples, leads 20 may include sensing electrodes positioned to detect an EEG signal within one or more region of patient's brain 12. Alternatively, another set of sensing electrodes may monitor the EEG signal. In some cases, EEG signals from within brain 16 may indicate the occurrence of seizure. Electrodes implanted closer to the target region of brain 12 may help generate an EEG signal that provides more useful information than an EEG generated via a surface electrode array because of the proximity to the target region of brain 12. The EEG signal that is generated from implanted electrode array may also be referred to as an electrocorticography (ECoG).

As described in further detail with reference to FIG. 2, IMD 16 includes a therapy module that generates the electrical stimulation delivered to patient 14 via leads 20. A signal generator (not shown) within IMD 16 produces the stimulation in the manner defined by the therapy program or group of programs selected by the clinician and/or patient 14. Generally, the signal generator is configured to produce electrical pulses to treat patient 14. However, the signal generator of IMD 16 may be configured to generate a continuous wave signal, e.g., a sine wave or triangle wave. In either case, IMD 16 generates the electrical stimulation therapy for DBS according to therapy parameters selected at that given time in therapy.

In the example shown in FIG. 1, IMD 16 generates the electrical stimulation according to one or more therapy parameter values, which may be arranged in a therapy program (or a parameter set). The therapy program includes a value for a number of parameters that define the stimulation. For example, the therapy parameter values may define respective values for voltage or current pulse amplitudes, pulse widths, pulse rates, pulse frequencies, electrode combinations, and the like. IMD 16 may store a plurality of programs. In some cases, the one or more stimulation programs are organized into groups, and IMD 16 may deliver stimulation to patient 14 according to a program group. During a trial stage in which IMD 16 is evaluated to determine whether IMD 16 provides efficacious therapy to patient 14, the stored programs may be tested and evaluated for efficacy.

IMD 16 may include a memory to store one or more therapy programs (e.g., arranged in groups), and instructions defining the extent to which patient 14 may adjust therapy parameter values, switch between programs, or undertake other therapy adjustments. Patient 14 may generate additional programs for use by IMD 16 via patient programmer 24 at any time during therapy or as designated by the clinician.

Generally, an outer housing of IMD 16 is constructed of a biocompatible material that resists corrosion and degradation from bodily fluids. In some examples, IMD 16 may be implanted within a subcutaneous pocket close to the stimulation site. Although IMD 16 is shown as implanted within patient 14 in FIG. 1, in other examples; IMD 16 may be located external to patient 14. For example, IMD 16 may be a trial stimulator electrically coupled to one or more percutaneous leads during a trial period. If the trial stimulator indicates therapy system 10 provides effective treatment to patient 14, the clinician may implant a chronic stimulator within patient 14 for long-term treatment.

Clinician programmer 22 may be a computing device including, for example, a PDA, a laptop computer, a desktop PC, a workstation, and the like that permits a clinician to program electrical stimulation therapy for patient 14, e.g., using input keys and a display. For example, using clinician programmer 22, the clinician may specify therapy programs that include one or more therapy parameter values and/or organize the therapy programs into therapy program groups (i.e., groups including one or more therapy parameters) for use in delivery of DBS. Clinician programmer 22 supports telemetry (e.g., radio frequency (RF) telemetry) with IMD 16 to download stimulation parameters and, optionally, upload operational or physiological data stored by IMD 16. In this manner, the clinician may periodically interrogate IMD 16 to evaluate efficacy and, if necessary, modify the stimulation parameters.

Like clinician programmer 22, patient programmer 24 may be a handheld computing device. Patient programmer 24 may also include a display and input keys to allow patient 14 to interact with patient programmer 24 and IMD 16. In this manner, patient programmer 24 provides patient 14 with an interface for limited control of electrical stimulation therapy provided by IMD 16. For example, patient 14 may use patient programmer 24 to start, stop or adjust electrical stimulation therapy. In particular, patient programmer 24 may permit patient 14 to adjust stimulation parameters such as duration, amplitude, pulse width and pulse rate within an adjustment range specified by the clinician via clinician programmer 22, select from a library of stored stimulation therapy programs, or reset the current therapy cycle.

As described in further detail below, patient programmer 24 includes an event indication input mechanism that patient 14 may activate in order to provide input to programmer 24 indicating that a patient event has occurred. The patient event may include, for example, a detection of a symptom of the patient's condition. As one example of the use of the event indication input mechanism, when patient 14 begins sensing an aura, which is a symptom for some patients that occurs prior to the actual onset of a severe seizure, patient 14 may activate the event indication button, e.g., by depressing a button. An aura may be indicated by a wide range of symptoms including, for example, lightheadedness, dizziness, unusual smells, unusual emotions, altered vision and hearing, and the like. In response to patient 14 activating the event indication button of programmer 24, patient programmer 24 may record a time stamp indicating the time and date when the event indication input mechanism was activated. In some examples, patient programmer 24 may provide a signal to IMD 16 that causes IMD 16 to initiate therapy delivery, modify at least one therapy parameter, or reset therapy in response to receiving the indication from patient 14 via the event indication button.

While the event indication input mechanism is primarily referred to as an "event indication button" throughout the remainder of the disclosure, the disclosure is not so limited. In other examples, the event indication input mechanism may be any suitable input mechanism, such as a push button, a softkey, a voice activated command, a means activated by other physical interactions, a magnetically triggered switch, a contact defined by a touch screen, or any other suitable input mechanism that patient 14 may activate in order to indicate that patient 14 believes a seizure may occur.

Patient programmer 24 may also include other input mechanisms to allow patient 14 to enter information related to an event. For example, any of the above-listed input mechanisms may be used to enter information including, but not limited to, the type or severity of the seizure, the duration of the seizure, the efficacy of a therapy provided during, before or after the seizure, the drug taken prior to or after the event, and the like. Patient programmer 24 may then associate this entered information with an event indication button press, and store the information in memory for subsequent downloading and viewing using clinician programmer 22, or for later viewing using patient programmer 24. In this way, patient programmer 24 may receive and record information specifying the impact therapy system 10 may have had on the patient event and/or patient condition.

Clinician programmer 22 may be used to program and/or interrogate IMD 16 and patient programmer 24, as described in further detail below. For example, clinician programmer 22 may download event information stored in IMD 16 or patient programmer 24. The event information may be entered by patient 14, or may be collected by IMD 16 using sensors communicatively coupled to IMD 16. In some examples, clinician programmer 22 may present the event information to a clinician in textual form, such as a list or table, or in graphical form, including Venn diagrams, bar graphs, line graphs, and the like.

IMD 16, clinician programmer 22, and patient programmer 24 may communicate with each other via cables or a wireless communication, as shown in FIG. 1. Clinician programmer 22 and patient programmer 24 may communicate, for example, via wireless communication with IMD 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 2:
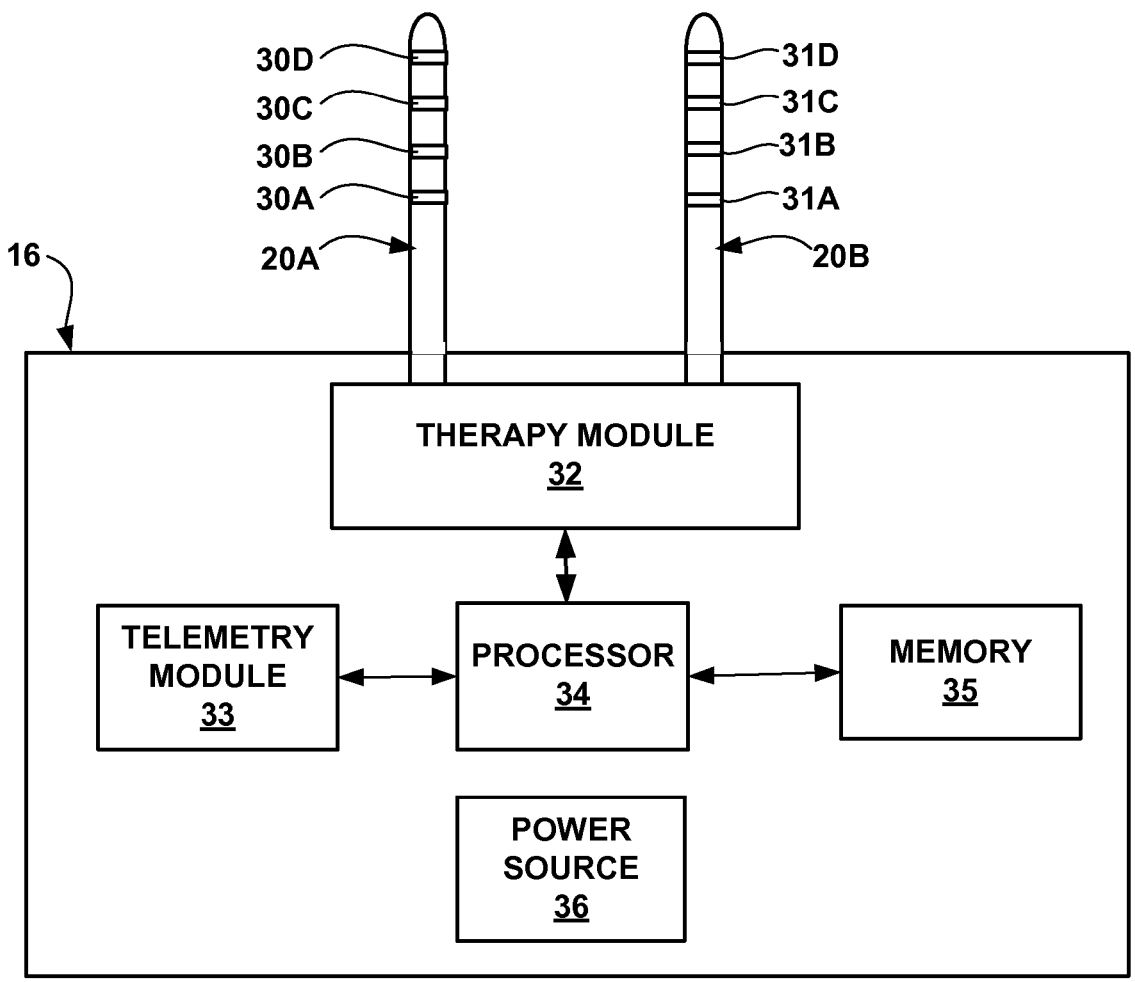
FIG. 2 is a schematic block diagram illustrating example components of the implantable medical device of FIG. 1.

FIG. 2 is a functional block diagram illustrating components of an example IMD 16 in further detail. IMD 16 is coupled to leads 20A and 20B, which include electrodes 30A-D and 31A-D, respectively. Although IMD 16 is coupled directly to leads 20, in other examples, IMD 16 may be coupled to leads 20 indirectly, e.g., via lead extension 18 (FIG. 1). IMD 16 includes a therapy module 32, a telemetry module 33, a processor 34, memory 35, and a power source 36.

IMD 16 may deliver electrical stimulation therapy to brain 12 of patient 14 via electrodes 30A-D of lead 20A and electrodes 31A-D of lead 20B (collectively "electrodes 30 and 31"). In the example shown in FIG. 2, implantable medical leads 20 are cylindrical. As previously described, in other examples, leads 20 may be, at least in part, paddle-shaped (i.e., a "paddle" lead) or a shape other than cylindrical. In some examples, electrodes 30 and 31 may be ring electrodes. In other examples, electrodes 30 and 31 may be segmented or partial ring electrodes, each of which extends along an arc less than 360 degrees (e.g., 90-120 degrees) around the outer perimeter of the respective one of leads 20. The use of segmented or partial ring electrodes 30 and 31 may also reduce the overall power delivered to electrodes 30 and 31 by IMD 16 because of the efficient delivery of stimulation to a target stimulation site by eliminating or minimizing the delivery of stimulation to unwanted or unnecessary regions within patient 14. The configuration, type, and number of electrodes 30 and 31 illustrated in FIG. 2 are merely exemplary. In other examples, IMD 16 may be coupled to one lead, more than two leads or leads including less than or more than four electrodes. For example, IMD 16 may be coupled to one lead with eight electrodes on the lead or three or more leads with the aid of bifurcated lead extensions.

Electrodes 30 and 31 are electrically coupled to therapy module 32 of IMD 16 via conductors within the respective leads 20A and 20B. Each of electrodes 30 and 31 may be coupled to separate conductors so that electrodes 30 and 31 may be individually selected, or in some examples, two or more electrodes 30 and/or two or more electrodes 31 may be coupled to a common conductor. In one example, an implantable signal generator or other stimulation circuitry within therapy module 32 delivers electrical signals (e.g., pulses or substantially continuous-time signals, such as sinusoidal signals) to a target tissue site within patient 14 via at least some of electrodes 30 and 31 under the control of processor 34. The stimulation energy generated by therapy module 32 may be delivered from therapy module 32 to selected electrodes 30 and 31 via a switch matrix and conductors carried by leads 20, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like. The functions attributed to processor 34 herein may be embodied as software, firmware, hardware or any combination thereof. Processor 34 controls the implantable signal generator within therapy module 32 to deliver electrical stimulation therapy according to selected therapy parameter values. For example, processor 34 may control therapy module 32 to deliver electrical signals with selected voltage or current amplitudes, pulse widths (if applicable), and rates specified by one or more therapy programs, which may be arranged into therapy program groups. In one example, processor 34 controls therapy module 32 to deliver stimulation therapy according to one therapy program group at a time. The therapy programs and therapy program groups may be stored within memory 35. In another example, therapy programs are stored within at least one of clinician programmer 22 or patient programmer 24, which transmits the therapy programs to IMD 16 via telemetry module 33.

In addition, processor 34 may also control therapy module 32 to deliver the electrical stimulation signals via selected subsets of electrodes 30 and 31 with selected polarities. For example, two of more of electrodes 30 and 31 may be utilized together in various bipolar or multi-polar combinations to deliver stimulation energy to selected sites, such as sites within brain 12. The above-mentioned switch matrix may be controlled by processor 34 to configure electrodes 30 and 31 in accordance with a therapy program.

IMD 16 also includes memory 35, which may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 35 may store program instructions that, when executed by processor 34, cause IMD 16 to perform the functions ascribed to IMD 16 herein. In some examples, memory 35 may also store the parameter values for therapy programs or program groups and/or patient physiological data obtained by sensors communicatively coupled to IMD 16 or another sensing device.

Telemetry module 33 includes any suitable hardware, firmware, software or any combination thereof for communicating with another device, such as clinician programmer 22 or patient programmer 24 (FIG. 1). Under the control of processor 34, telemetry module 33 may receive downlink telemetry from and send uplink telemetry to at least one of the programmers 22, 24 with the aid of an antenna, which may be internal and/or external. Processor 34 may provide the data to be uplinked to at least one of the programmers 22, 24 and the control signals for the telemetry circuit within telemetry module 33, e.g., via an address/data bus.

The various components of IMD 16 are coupled to power source 36, which may include a rechargeable or non-rechargeable battery. A non-rechargeable battery may be selected to last for several years, while a rechargeable battery may be inductively charged from an external device, e.g., on a daily or weekly basis.

Figure 3:
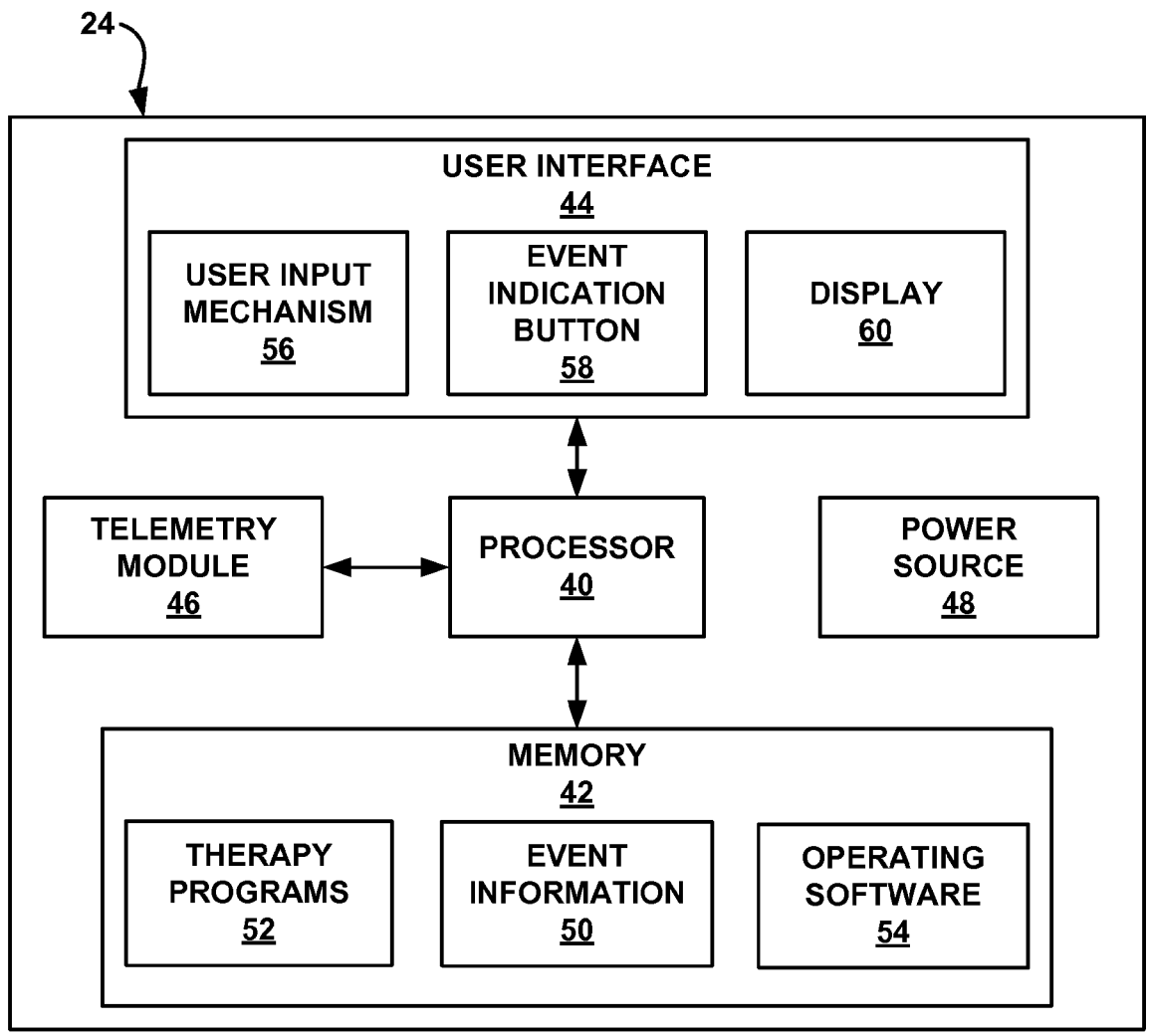
FIG. 3 is a schematic block diagram illustrating example components of the patient programmer of FIG. 1.

FIG. 3 is a functional block diagram illustrating components of an example patient programmer 24, which includes a processor 40, memory 42, a user interface 44, a telemetry module 46 and a power source 48. Processor 40 controls user interface 44 and telemetry module 46, and stores and retrieves information and instructions to and from memory 42. Patient programmer 24 may be a dedicated hardware device with dedicated software for programming of IMD 16. Alternatively, patient programmer 24 may be an off-the-shelf computing device running an application that enables programmer 24 to program IMD 16.

Patient 14 may use patient programmer 24 to select therapy programs (e.g., sets of stimulation parameters), generate new therapy programs, reset therapy programs or cycles, modify therapy programs through individual or global adjustments, and transmit the new programs to a medical device, such as IMD 16 (FIGS. 1 and 2). In addition, as described in further detail below, patient 14 may use patient programmer 24 to create a log of event occurrences, which may include actual seizure occurrences or potential seizure occurrences.

Patient 14 may interact with patient programmer 24 via user interface 44, which includes a user input mechanism 56, an event indication button 58, and a display 60. User input mechanism 56 may include any suitable mechanism for receiving input from patient 14 or another user. In one example, user input mechanism includes an alphanumeric keypad. In another example, user input mechanism 56 includes a limited set of buttons that are not necessarily associated with alphanumeric indicators. For example, the limited set of buttons may include directional buttons that permit patient 14 to scroll up, down, or sideways through a display presented on display 60, select items shown on display 60, as well as enter information. As another example, the limited set of buttons may also include "increment/decrement" buttons in order to increase or decrease a stimulation frequency or amplitude of stimulation delivered by IMD 16.

User input mechanism 56 may include any one or more of push buttons, soft-keys, voice activated commands, activated by physical interactions, magnetically triggered, activated upon password authentication push buttons, contacts defined by a touch screen, or any other suitable user interface. In some examples, one or more button of user input mechanism 56 may be reprogrammable. That is, during the course of use of patient programmer 24, one or more button of user input mechanism 56 may be reprogrammed to provide different programming functionalities as the needs of patient 14 change or if the type of IMD 16 implanted within patient 14 changes. User input mechanism 56 may be reprogrammed, for example, by clinician programmer 22 (FIG. 1) or another computing device.

Event indication button 58 may be any one or more of a push button, soft-key, voice activated command, means activated by another physical interaction, magnetically triggered switch, activated upon password authentication push button, contact defined by a touch screen, or any other suitable input mechanism. In the example shown in FIG. 3, event indication button 58 is a dedicated button that is separate from the buttons of user input mechanism 56 in order to allow patient 14 to quickly access and activate event indication button 58. In other examples, however, event indication button 58 may be incorporated with the buttons of user input mechanism 56. For example, if user input mechanism 56 includes a plurality of alphanumeric buttons, depressing one or more of the buttons in a particular pattern or pushing two or more of the buttons simultaneously may also trigger the functionality of event indication button 58.

Patient 14 may "activate" event indication button 58 by depressing a push button, soft-key, touching the corresponding portion of a touch screen of display 60 or using any other suitable techniques. A soft-key may include a button or a key of a device, where the button or key is associated with a label presented on display 58. As the label on display 58 changes, the functionality of the soft-key changes. Event indication button 58 is coupled to processor 40. After patient 14 activates event indication button 58, processor 40 may generate an event marker. The event marker may be, for example, a value, flag or signal that is stored by processor 46 within event information 50 of memory 42. If patient 14 is afflicted with seizures, the event marker may also be referred to as a "seizure marker."

In different examples, the generation of the event marker may result in the performance of different subsequent actions by patient programmer 24. The event marker may also result in patient programmer 24 performing two or more of these actions described herein. In one example, processor 40 logs the date and time of each event marker within event information 50 of memory 42. The event marker is indicative of the event occurrence (e.g., either actual or potential seizure) as perceived by patient 14. In this way, the event indication button 58 may be used to create an event log, such as a log that details the occurrence of each seizure or seizure symptom.

A clinician may access the event log and analyze the event log to evaluate various aspects of the patient's condition or therapy system 10. For example, the clinician may review the event log to determine a temporal pattern in the event occurrences. This may allow a clinician to determine, for example, that the events are being influenced or triggered by a certain factor, such as stress at the patient's home or office. In some cases, processor 40 associates the event marker with the current therapy program or program group that is being implemented by IMD 16 in order to evaluate the efficacy of the current therapy program or group. Processor 40 may determine the current therapy program implemented by IMD 16 by interrogating IMD 16 via the respective telemetry modules 33, 46. Alternatively, the current therapy program implemented by IMD 16 may be stored within therapy programs 52 of memory 42 of patient programmer 24.

IMD 16 may be configured to sense and record physiological parameter values of patient 14. For example, leads 20 may include sense electrodes or another sensor that are electrically coupled to therapy module 32, which includes sensing functionality. As another example, in addition to or instead of an IMD 16 including sensing capabilities, a separate sensor may be implanted within patient 14 and transmit sense information to IMD 16, e.g., via a wired or wireless communication technique. In either case, IMD 16 may receive physiological parameter values of patient 14 and transmit the physiological parameter values to patient programmer 24, and processor 40 may associate the event marker with the physiological parameter values and store the data within event information 50 of memory 42. In this way, the event information may include physiological parameter values sensed by IMD 16 or another sensing device. In some examples, the physiological parameters at the time the event marker was generated, as well as the physiological parameter values during a certain time period before and after the event marker generation may be recorded within event information 50. The clinician may determine the relevant range of time for which the physiological parameter values are stored.

Alternatively, IMD 16 may receive the event marker from patient programmer 24 and store the marker along with the associated physiological parameter values within memory 35 (FIG. 2). In another example, processor 40 of programmer 24 may generate a record signal that causes IMD 16 to store the current physiological parameter values, and, in some cases, the parameter values within a particular time span prior to receiving the record signal (e.g., about two seconds to about one minute). Patient programmer 24 may also record the date and time of the event marker, and a clinician may later retrieve the data from patient programmer 24 and IMD 16 and associate the event marker with the patient parameter values, either manually or with the aid of a computing device, such as clinician programmer 22.

In another example, upon the generation of the event marker, processor 40 may transmit the event marker to IMD 16 via telemetry module 46, and IMD 16, in response, may modify therapy. For example, in response to receiving the event marker from patient programmer 24, IMD 16 may initiate therapy or restart a therapy cycle. In this way, the event marker may be a signal that controls the operation of IMD 16. The settings for IMD 16 necessary to initiate or restart the therapy cycle (i.e., the therapy adjustment action) may be saved within therapy programs 52 of memory 42 of patient programmer 24 or within memory 35 of IMD 16. If the settings are stored within IMD 16, processor 40 may provide instructions to IMD 16 to access and implement the stored therapy adjustment action.

In some examples, processor 40 may generate different types of event markers that provide different control signals to IMD 16. As an example, a first type of event marker may be a control signal that causes IMD 16 to restart a therapy cycle and a second type of event marker may be a control signal that causes IMD 16 to switch to a different therapy program group stored within memory 35 of IMD 16 or memory 42 of programmer 24. However, the event markers do not necessarily need to directly provide a control signal. Rather, processor 40 of programmer 24 or processor 34 of IMD 16 may generate the necessary control signal based on the event marker.

In yet another example, generation of the event marker may result in the creation of a new data file stored in the event information 50 section of memory 42 that is editable by a user, including patient 14 or a clinician. For example, the data file may include data fields that store information about the patient's therapy or the patient event. As examples, the data file may include information about the type or severity of a seizure, the duration of the seizure, the efficacy of therapy, the drug and/or drug dosage being taken prior to or after the seizure, and the like. User input mechanism 56 may allow patient 14 to enter the relevant information at any time following the generation of the event marker and the creation of the data file. For example, in the case of an event related to a seizure, patient 14 may enter information relating to the seizure following recovery from the seizure event, and may edit the information during some time period following the initial entry of the data.

As indicated above, one or more of the features described above may be combined in a single example. For example, activating event indication button 58 may reset the current therapy delivered by IMD 16, generate an event marker in event information 50, create a data file associated with the event marker in event information 50, and store physiological parameter values collected by IMD 16 the data file, or another data file also associated with the event marker.

Event indication button 58, as well as other input mechanisms provided by user input mechanism 56 may be may be designed to help reduce accidental activation of a programming function. For example, the button 58 may be recessed from an outermost surface of the housing of IMD 24. Alternatively or additionally, patient 16 may be required to hold a button for a predetermined amount of time in order to activate the button, and/or there may be a hold function that prevents the buttons from being activated unless the hold function is deactivated. For example, the hold function may be activated and deactivated via manipulation of a slider bar (not shown) or manipulation of a specified combination of buttons.

Display 60 may include a color or monochrome display screen, such as a liquid crystal display (LCD), light emitting diode (LED) display or any other suitable type of display. Patient programmer 24 may present information related to stimulation therapy provided by IMD 16 on display 60, as well as other information, such as historical data regarding the patient's condition and past event information. Processor 40 may monitor activity from user input mechanism 56, and control display 60 and/or IMD 16 function accordingly. In some examples, display 60 may be a touch screen that enables the user to select options directly from the display. In such cases, user input mechanism 56 may be eliminated, although patient programmer 24 may include both a touch screen and user input mechanism 56. In some examples, user interface 44 may also include audio circuitry for providing audible instructions or sounds to patient 14 and/or receiving voice commands from patient 14.

Processor 40 may comprise any combination of one or more processors including one or more microprocessors, DSPs, ASICs, FPGAs, or other equivalent integrated or discrete logic circuitry. Accordingly, processor 40 may include any suitable structure, whether in hardware, software, firmware, or any combination thereof, to perform the functions ascribed herein to processor 40. Memory 42 may include any volatile or nonvolatile memory, such as RAM, ROM, EEPROM or flash memory. Memory 42 may also include a removable memory portion that may be used to provide memory updates or increases in memory capacities. A removable memory may also allow patient data to be easily transferred to clinician programmer 22, or to be removed before patient programmer 24 is used by a different patient.

Memory 42 stores, among other things, event information 50, therapy programs 52, and operating software 54. Memory 42 may have any suitable architecture. For example, memory 42 may be partitioned to store event information 50, therapy programs 52, and operating software 54. Alternatively, event information 50, therapy programs 52, and operating software 54 may each include separate memories that are linked to processor 40. In some examples, event information 50 may store event information in different resolutions. For example, relatively recent event information may be stored in detail by individual event, while less recent event information may be aggregated and stored in week resolution, month resolution, or any other time period resolution specified by a user, such as a clinician. The differentiation in resolution based on the type of information may be an efficient use of memory 42, which may have a limited capacity to store information.

Therapy programs 52 portion of memory 42 stores data relating to the therapy programs implemented by IMD 16. In some examples, the actual parameter values for the therapy programs, e.g., the stimulation amplitude, pulse rate, pulse frequency and pulse width data, are stored within therapy programs 52. In other examples, an indication of each therapy program or group of therapy programs, e.g., a single value associated with each therapy program or group, may be stored within therapy programs 52, and the actual parameter values may be stored within memory 35 of IMD 16. The "indication" for each therapy program or group may include, for example, alphanumeric indications (e.g., Therapy Program Group A, Therapy Program Group B, and so forth), or symbolic indications.

As previously described, event information 50 includes information relating to the patient event (seizure or anticipated seizure) occurrences, such as the time and date patient 14 activated the event indication button 58, and corresponding physiological parameter values (e.g., EEG signals, ECG signals, respiratory signals, blood pressure, body temperature, and so forth), if therapy system 10 includes a sensing module and sensors to sense such physiological parameters. Patient programmer 24 may also receive input from patient 14 relating to event information, such as the type or severity of the seizure, the duration of the seizure, and any drugs, taken after patient 14 activated seizure indication button 58. This information, as well as any other applicable information, may also be stored within event information 50 and, in some cases, associated with the event marker.

Operating software 54 may include instructions executable by processor 40 for operating user interface 44, telemetry module 46 and managing power source 48. Memory 42 may also store any therapy data retrieved from IMD 16 during the course of therapy. The clinician may use this therapy data to determine the progression of the patient's disease in order to predict or plan a future treatment.

Patient programmer 24 may communicate via wireless telemetry with IMD 16, such as using RF communication or proximal inductive interaction. This wireless communication is possible through the use of the respective telemetry modules 46, 33. Accordingly, telemetry module 46 of programmer 24 may be similar to the telemetry module contained within IMD 16. Telemetry module 46 may also be configured to communicate with clinician programmer 22 or another computing device via wireless communication techniques, or direct communication through a wired connection. Examples of local wireless communication techniques that may be employed to facilitate communication between patient programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 24 without needing to establish a secure wireless connection.

Power source 48 delivers operating power to the components of patient programmer 24. Power source 48 may include a battery and a power generation circuit to produce the operating power. In some examples, the battery may be rechargeable to allow extended operation. Recharging may be accomplished electrically coupling power source 48 to a cradle or plug that is connected to an alternating current (AC) outlet. In addition, recharging may be accomplished through proximal inductive interaction between an external charger and an inductive charging coil within patient programmer 24. In other examples, traditional batteries (e.g., nickel cadmium or lithium ion batteries) may be used. In addition, patient programmer 24 may be directly coupled to an alternating current outlet recharge power source 48, or to power patient programmer 24. Power source 48 may include circuitry to monitor power remaining within a battery. In this manner, user interface 44 may provide a current battery level indicator or low battery level indicator when the battery needs to be replaced or recharged. In some cases, power source 48 may be capable of estimating the remaining time of operation using the current battery.

User interface 44 may include an alert LED or other suitable alert feature. In some examples, IMD 16 may send an alert signal to patient programmer 24 via the respective telemetry modules 33, 46 to activate the alert LED and indicate to a user that a problem may be present. The alert signal may, for example, signify a low battery, a sensed physiological event, or another problem. For example, the alert feature of user interface 44 may be triggered in response to receiving a threshold number of event indications via event indication button 56, detecting a change in a therapy program or another therapy parameter. As another example, if IMD 16 is configured to deliver a drug to patient 16 instead of or in addition to electrical stimulation, the alert feature of user interface 44 of patient programmer 24 may be triggered in response to detecting a low level of drug remaining, or to indicate the delivery of a more powerful anti-seizure drug. Activation of the alert feature of patient programmer 24 may alert patient 16 to contact a clinician or take other precautions. In some examples, patient programmer 24 may forward the alert or an indication of the alert to a remote device in a remote location, such as a clinician office.

User interface 44 may also include an LED or another indication (e.g., via display 60) that provides confirmation to patient 14 that an operation was carried out or that input via event indication button 58 was received. For example, when event indication button 58 is activated by patient 14, and a programming signal is sent to IMD 16 to reset a therapy cycle, adjust a therapy parameter, switch to a different therapy program or program group, or otherwise adjust therapy, user interface 44 may activate an LED to provide positive feedback to patient 14 regarding the successfully sent programming signal.

Figure 4:
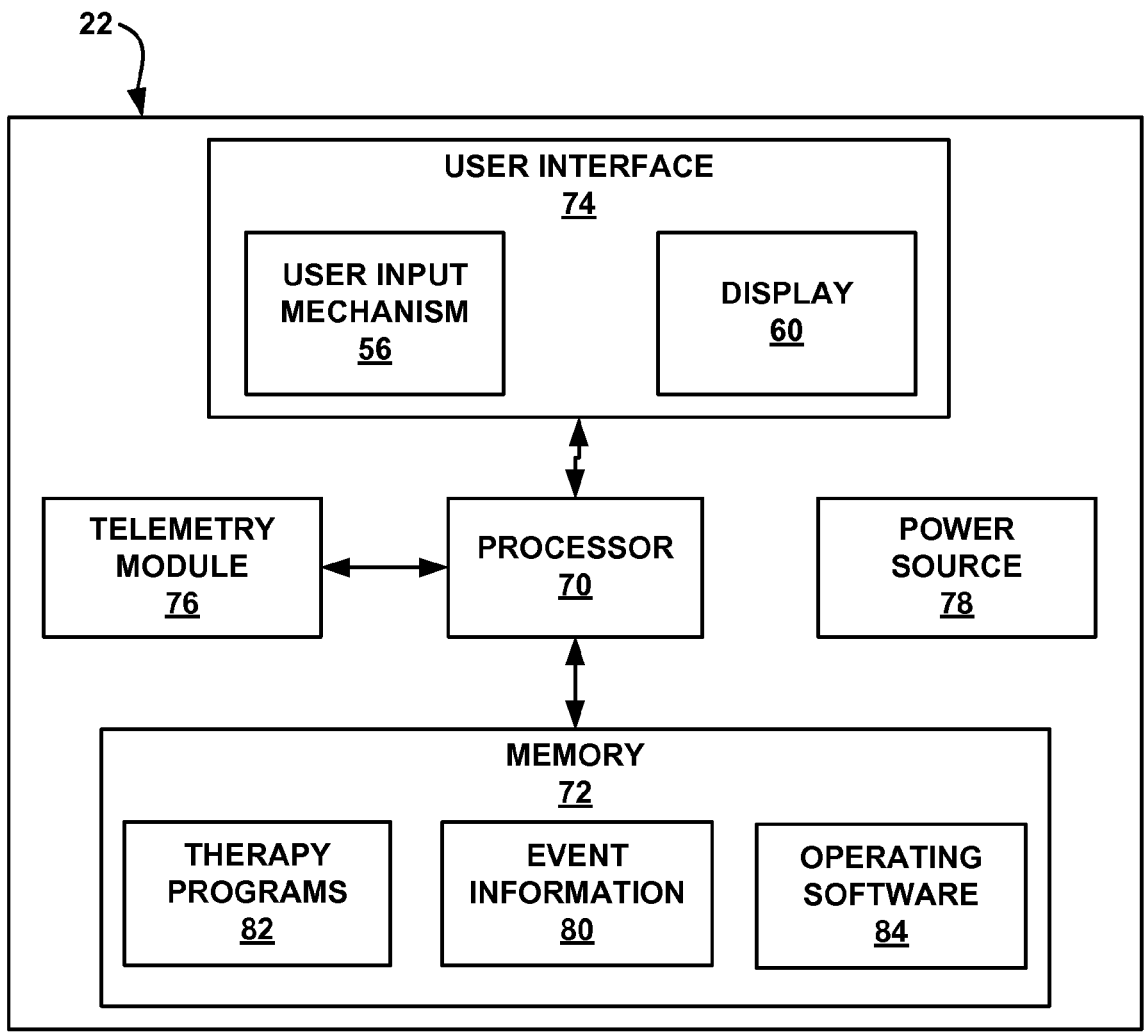
FIG. 4 is a schematic block diagram illustrating example components of the clinician programmer of FIG. 1.

FIG. 4 is a functional block diagram illustrating components of an example clinician programmer 22, which may be similar to patient programmer 24, but does not include seizure indication button 58. Clinician programmer 22 may include a processor 70, memory 72 that stores therapy programs 82, event information 80, and operating software 84, user interface 74 including user input mechanism 56 and display 60, telemetry module 76, and power source 78. The functions performed by each component may be similar to the functions described above with reference to patient programmer 24. Additionally, clinician programmer 22 may include more features than patient programmer 24. For example, while clinician programmer 22 may be configured for more advanced programming features than patient programmer 24. This may allow a user to modify more therapy parameter values with clinician programmer than with patient programmer 24. Patient programmer 24 may have a relatively limited ability to modify therapy parameter values of IMD 16 in order to minimize the possibility that patient 14 selects therapy parameters that are harmful to patient 14. Similarly, clinician programmer 22 may conduct more advanced diagnostics of IMD 16 than patient programmer 24.

As described in further detail below, processor 70 of clinician programmer 22 may interrogate IMD 16 and/or patient programmer 24 to retrieve any collected information stored within memories 35, 42, such as event markers, physiological parameter values, and information associated with respective event markers, which may include information received from patient 14. For example, memory 72 of clinician programmer 22 may include software including instructions that cause processor 70 of clinician programmer 22 to interrogate IMD 16 and/or patient programmer 24.

Processor 70 of clinician programmer 22 may format the collected information in any one of a plurality of information presentation techniques, such as a linear format (e.g., tables or lists) or graphical displays (e.g., line graphs, bar graphs, pie charts, Venn diagrams, histograms, and the like), either automatically or at the request of a clinician. Display of the collected information in one or more of these display types may enable a clinician to more easily determine the efficacy of therapy provided to patient 14, and identify any trends in the efficacy of therapy, such as decreasing effectiveness of a drug or stimulation program over time. In some examples, patient programmer 24 may also display the collected information in formats similar to clinician programmer 22.

Figure 5:
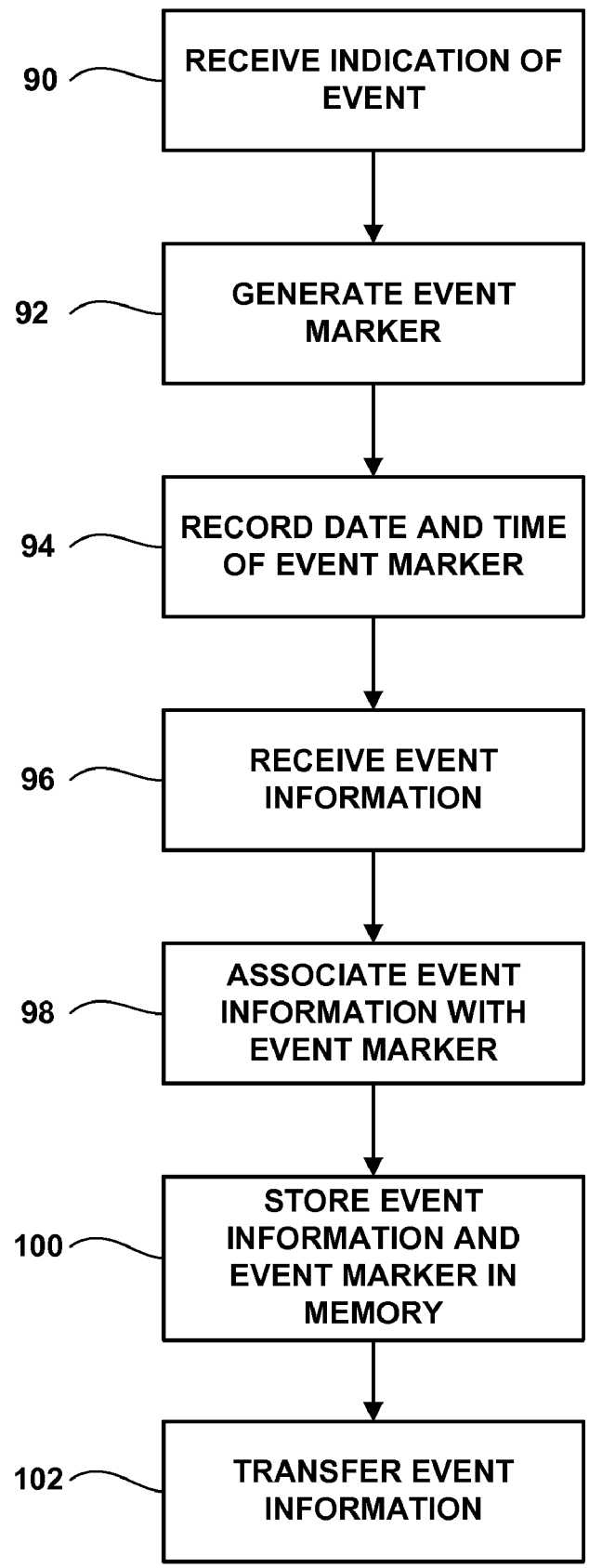
FIG. 5 is a flow diagram illustrating an example technique that includes recording seizure information.

FIG. 5 is a flow diagram illustrating an example method for storing patient event information on patient programmer 24. Patient 14 may detect the occurrence of an event related to a patient condition. In the case of a seizure, for example, patient 14 may sense an aura, which may be, in some cases, a precursor to a tonic-clonic seizure. An aura may be a simple partial seizure, and may be indicated by a wide range of symptoms including, for example, lightheadedness, dizziness, unusual emotions, altered vision and hearing, and the like. When patient 14 perceives an aura, patient 14 may provide an indication to patient programmer 24 by, for example, activating event indication button 58 (90). Processor 40 of patient programmer 24 is coupled to event indication button 58, and, therefore, receives the indication of the event (90), and generates an event marker (92). As previously described, the event marker may be a flag, value or other signal. Processor 40 may record the date and time of the event marker within event information 50 of memory 42 of patient programmer 24 (94), which may be, for example, the date and time processor 40 generated the event marker.

The resolution of the time and date stamp of the event marker may be on the order of seconds, for example, or may be less accurate, such as on the order of five minute increments, fifteen minute increments, or even hour increments. The time accuracy may be programmed by the clinician, or may be preprogrammed into patient programmer 24. Recording the time and date that each event marker was generated by processor 40 may indicate each time patient 14 activated the event indication button 58. A clinician may later reference the event markers to determine any patterns or trends in the occurrence of patient events. For example, events occurring repeatedly at approximately the same time of day may indicate an emotional triggering of the event, such as stress at work or school.

Generation of an event marker may also cause patient programmer 24 to query IMD 16 and record the therapy program or group of programs being implemented by IMD 16 at the time processor 40 generated the event marker. Alternatively, patient programmer 24 may transmit the event marker to IMD 16, which may associate the event marker with a current therapy program or group. Depending upon the type of IMD 16 or the mode of operation of IMD 16, in some cases, processor 40 may associate the event marker with a single therapy program, rather than a program group, which may include one or more therapy programs. Thus, while program groups are primarily referred to throughout the description of FIG. 5, in other examples, processor 40 may associate the event marker with a therapy program.

As previously described, processor 40 may interrogate IMD 16 to determine which program group IMD 16 is currently delivering therapy in accordance with, or processor 40 may track the current program group within therapy programs 52 portion of memory 42. Patient 14 may not activate event indication button 58 as soon as the patient event occurs. For example, if a patient 14 is struck with a seizure, patient 14 may not be able to activate event indication button 58 until after patient 14 recovers from the seizure, which may be well after the occurrence of the seizure. For example, depending upon the duration and severity of the seizure, recovery may take minutes or even hours. Thus, processor 40 may associate the event marker with the most recently implemented therapy program or the currently implemented therapy program. Alternatively, patient programmer 24 may provide patient 14 with the opportunity to modify the date and time of the event marker. If patient 14 knew, for example, that the event occurred at least two hours before patient 14 actually activated event indication button 58, patient 14 may modify the time of the event marker by at least two hours via user input mechanism 56 (FIG. 3).

As described briefly above, in some examples in which IMD 16 provides therapy in accordance with a therapy cycle, the therapy cycle is reset when patient 14 activates event indication button 58. In one example, an electrical stimulation program may comprise a therapy cycle including an on-cycle, in which stimulation is delivered to patient 14, and an off-cycle, in which no stimulation is delivered to patient 14. However, IMD 16 typically does not shut down during stimulation off-cycle, but rather, therapy module 32 of IMD 16 merely stops delivering stimulation to patient 14. In some examples, a minimum level of stimulation is provided to patient during the stimulation off-cycle, and the intensity of the stimulation increases during the stimulation on-cycle. Depending upon the patient disorder, it may be undesirable to completely turn stimulation off.

As one example of resetting a therapy cycle, if the event indication button is activated during an off-cycle portion of the therapy cycle, the current therapy cycle may be shortened as compared to a normal therapy cycle. The "normal" therapy cycle may include at least one on-cycle and at least one off-cycle. If the event indication button is received during an on-cycle, the therapy cycle may increase because the on-cycle increases. However, regardless of the shortened or elongated therapy cycles, subsequent therapy cycles return to the normal therapy cycle length. For example, using the therapy cycle including a one minute on-cycle and a five minute off-cycle as an example, if patient 14 activates event indication button 58 during the one minute on-cycle, processor 40 provides a control signal to IMD 16 or otherwise controls IMD 16 to restart the one minute on-cycle, regardless of the point during the one minute stimulation session the indication of the patient event was received.

In this way, patient 14 may directly affect the therapy cycle implemented by IMD 16 by activating event indication button 58. Furthermore, because IMD 16 maintains the same timing between an on-cycle and off-cycle, but only initiates or restarts the cycle upon generation of the event marker by processor 40, therapy system 10 remains an open loop system that provides stimulation in a regular cycle. Thus, after the therapy on-cycle is restarted, IMD 16 continues implementing the normal therapy cycle.

In some cases, resetting the therapy cycle implemented by IMD 16 may help prevent the onset of the seizure because therapy is essentially provided on demand, i.e., in response to the activation of event indication button 58. For example, if patient 14 senses an aura and activates event indication button 58, the delivery of therapy resulting from the resetting of the therapy cycle may prevent the aura from developing into a more severe seizure, such as a tonic-clonic seizure, or may lessen the duration or severity of the tonic-clonic seizure.

Regardless of whether processor 40 initiates adjustment of therapy in response to receiving an indication of the event via event indication button 58, patient 14 may enter information regarding the event and the efficacy of treatment (96) into programmer 24 at any time following the generation of the event marker. For example, if the aura does not develop into a more severe seizure, such as a tonic-clonic seizure, patient 14 may enter the data soon after activating event indication button 58 and the subsequent generation of the event marker. If, however, the aura does develop into a more severe seizure, such as a tonic-clonic seizure, patient 14 may enter the information at any time after recovering from the seizure.

Information may be input via user input mechanism 56 of patient programmer 24, as described in detail with reference to FIG. 3. Patient 14 may input the event information into patient programmer 24 by any suitable technique. As examples, patient 14 may select a predetermined entry from a list presented by a user interface of patient programmer 24, selecting an entry from a drop-down list presented by the user interface, selecting an icon presented by the user interface that represents the desired information, inputting text into patient programmer 24, and the like. An example of a user interface is described in further detail with reference to FIGS. 17A-17E.

The information that is inputted by patient 14 may include, for example, the seizure type or severity of the patient event. Seizure types may be categorized by the extent to which they affect the brain, the affect on a patient's consciousness, and the behavioral effects. For example, a partial seizure may only affect a localized area of brain 12 (FIG. 1), while a generalized seizure may affect both hemispheres of brain 12. Each of these major categories may be further broken up into a number of sub-categories such as, for example, simple partial seizures, complex partial seizures, absence seizures, tonic-clonic seizures, and the like. When a clinician programs patient programmer 24, the clinician may populate a list with the types of seizures patient 14 is most likely to experience or all available seizure types. The list may include a plurality of seizure types, such as less than five, five, or more than five. The clinician may also assign nicknames to each type of seizure according to terms with which patient 14 may be more familiar. For example, patient 14 may identify a tonic-clonic seizure as a "Severe Seizure" and an absence seizure as a "Short-term Seizure." Thus, the clinician and patient 14 may each use familiar language to identify the seizures. Further, in some examples, the list may include an editable option that allows a patient to enter a seizure type that is not otherwise included in the list.

Another exemplary type of event information input by patient 14 into patient programmer 24 may include the seizure duration. The seizure duration may be entered as any suitable time duration, such as, for example, five minute increments, or may be as accurate as patient 14 is able to determine. In some examples, patient programmer 24 may present a list including predetermined durations of time in order to provide a uniform time scheme. Seizure duration may be input via alphanumeric buttons, or may be selected from a dropdown list, a checkbox or the like.

Yet another example of information that may be inputted into patient programmer 24 by patient 14 may include an efficacy of the therapy. Efficacy of the therapy may refer to the patient's subjective rating of the general efficacy of therapy delivered via IMD 16. For example, patient 14 may assign an efficacy rating to the therapy program or program group implemented by IMD 16 at the time patient 14 perceived the patient event. In general, patient 14 may provide information that indicates whether the therapy delivered by IMD 16 was effective in prevent the patient event, reducing the severity or of the patient event, reducing the frequency of patient events, or reducing any residual effects of the patient event. In examples in which processor 40 of patient programmer 24 initiates the adjustment of one or more therapy parameter values or therapy cycles in response to the activation of event indication button 58, patient 14 may input information regarding the efficacy of the adjustments to therapy. Efficacy information may be especially useful in evaluating therapy system 10 in examples in which activating event indication button 58 resets the therapy cycle administered to patient 14 or initiates a change in the therapy program implemented by IMD 16.

In some examples, therapy efficacy information may not be immediately available. For example, patient 14 may not be able to discern between efficacious and non-efficacious therapy for a period of time after implantation of IMD 16 and commencement of therapy. In these examples, efficacy of the therapy may be determined by patient 14 after a plurality of patient events have occurred or after a sufficient time period of therapy delivery has passed.

In some examples, patient 14 may determine the efficacy of therapy by comparing the duration, severity or type of seizure that occurred after the adjustment to therapy or implementation of therapy system 10 to a baseline condition. The baseline condition may be, for example, the patient's condition prior to implementation of therapy system 10 or prior to the adjustment of therapy, if any, that was made in response to activating event indication button 58 (e.g., at substantially the same time the event marker was generated). In other examples, patient 14 may determine the efficacy of therapy based on the absence of a seizure after perception of an aura or a relatively less severe seizure (e.g., compared to prior seizures experienced by patient 14). Therapy efficacy information may be entered according to a numeric scale, for example, 1-5, where 1 indicates no seizure (a very efficacious therapy) and 5 indicates no change (non-efficacious therapy) or any other technique that indicates the relative effectiveness of therapy.

In some examples, patient programmer 24 may provide patient 14 with a user interface that permits patient 14 to input manually notes relating to event, and the notes may be associated with the event marker and stored within event information 50 portion of memory 42 (FIG. 3). For example, patient 14 may enter notes indicating an activity patient 14 was engaging in prior to perceiving an aura (e.g., exercise, eating, stressful situation, etc.), diet information, further description of the severity or type of the seizure, if one occurred, the effects of the seizure, or any other information patient 14 deems applicable to his therapy or condition.

As another example, patient 14 may enter information relating to the type or dosage of a drug or other pharmaceutical agent taken prior to the event or after a seizure occurred. Patient 14 may also input information specifying the time at which the drug or other pharmaceutical agent was ingested or otherwise received by patient 14. For example, patient 14 may take one anti-seizure drug in regular doses at consistent time intervals, and after a tonic-clonic seizure, patient 14 may ingest a more potent anti-seizure medication to prevent any additional seizures from occurring for an amount of time after the tonic-clonic seizure. In other examples, medication information may be stored in memory 35 of IMD 16 or memory 42 of patient programmer 24. Medication type and dosage may further help a clinician evaluate the efficacy of the currently prescribed therapy and determine if any changes to therapy are necessary and, if so, determine the nature of the changes.

After receiving event information (96), processor 40 of patient programmer 24 may associate the received event information with the corresponding event marker (98) and store the event marker and received information in event information 50 (100). Alternatively, processor 40 may transmit the information to IMD 16, which may store the data within memory 35. In some examples, processor 40 of patient programmer 24 may not immediately receive patient event information after the generation of the event marker. In those cases, processor 40 may associate the information received from patient 14 with the most recently generated event marker. In some examples, patient programmer 24 may display all or a portion of the event information associated with each of the event markers to patient 14, such as upon the request of patient 14. Displaying the event information to patient 14 may allow patient 14 to more closely monitor his or her therapy and condition.

In some examples, patient programmer 24 (or IMD 16) may store the event marker and event information until the subsequent clinic visit of patient 14. The clinician may review the event information and event markers to monitor the response of patient 14 to therapy, and, if necessary, generate a new treatment plan for patient 14. Upon interrogation by a computing device, such as clinician programmer 22, processor 40 of patient programmer 24 may control telemetry module 46 (FIG. 3) to transmit the event information and event marker to the computing device (102). Alternatively, processor 40 of patient programmer 24 may initiate the transmittal of the event information and associated event marker.

As discussed in more detail below, a clinician may manipulate and/or select areas of interest in the event information and clinician programmer 22 or another computing device may generate various displays of information, such as tables, bar graphs, Venn diagrams, and the like that present the event information in a more meaningful way. Graphical displays of information may reveal trends or other information useful to the clinician in treating patient 14. For example, event information may be viewed over a time period of multiple months, and a clinician may view the data to determine if a patient's response to a particular therapy parameter set is diminishing, or if the patient's response is unchanging or even improving.

Figure 6:
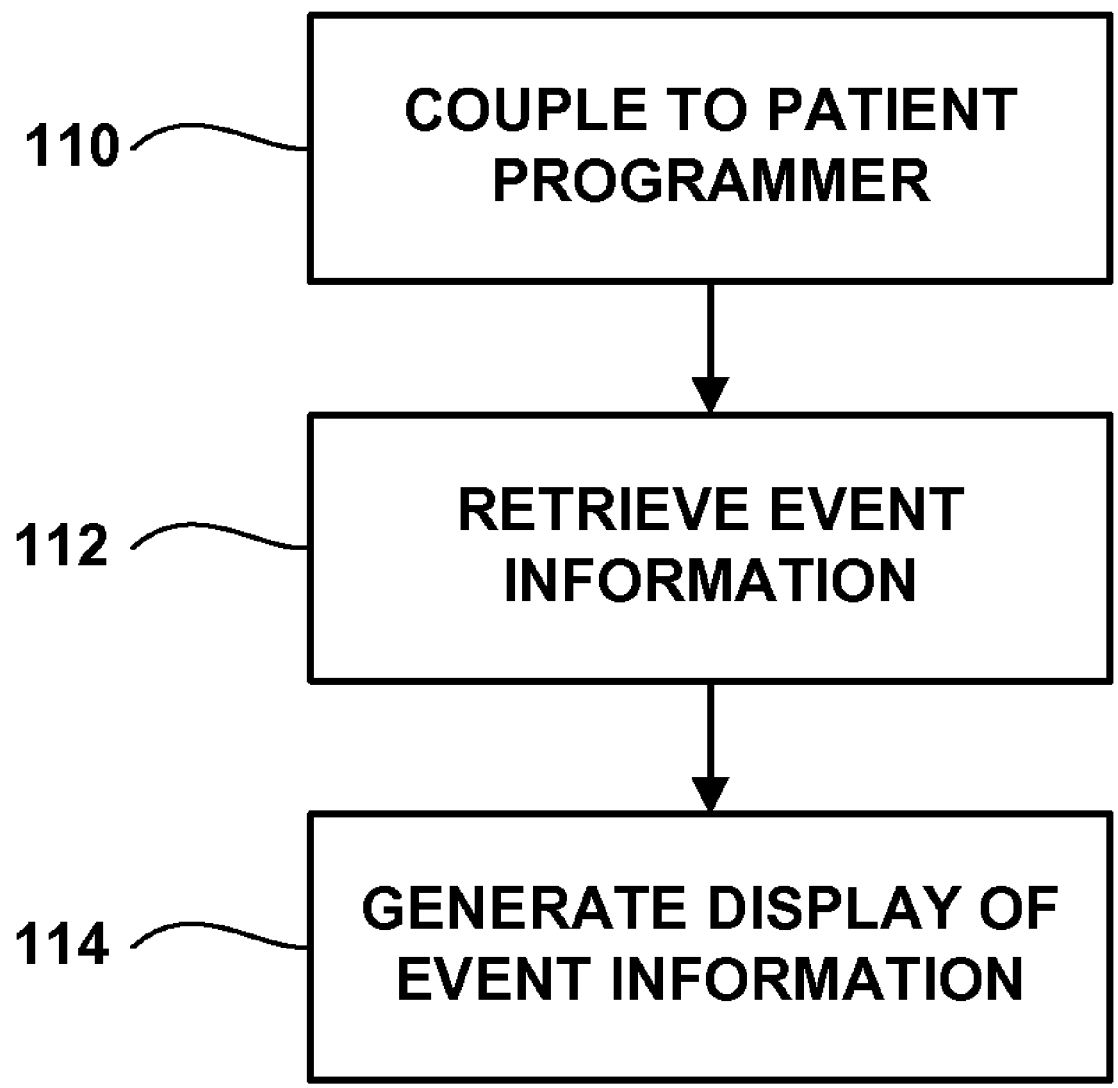
FIG. 6 is a flow diagram illustrating an example technique that includes obtaining and presenting event information to a user.

FIG. 6 is a flow diagram illustrating an example technique that a computing device, such as clinician programmer 22 or patient programmer 24, may employ to display event information received from patient 14 and/or physiological parameter sensors. While FIG. 6 is primarily described with reference to clinician programmer 22, in other examples, another computing device such as patient programmer 24 may perform any part of the technique shown in FIG. 6. Clinician programmer 22 may couple to patient programmer 24 through their respective telemetry modules 46 and 76 (110). Clinician programmer 22 may send a query or otherwise interrogate patient programmer 24 to retrieve event information stored in memory 42 of patient programmer 24 (112). In response to receiving the query, patient programmer 24 may transfer the event information (including the event marker) to clinician programmer 22.

After receiving the patient event information, processor 70 of clinician programmer 22 may format and display the event information (114). The event information may be displayed in a variety of display formats, including, for example, tables, lists, graphs, charts, and the like. Exemplary display formats will be described in more detail below with reference to FIGS. 8 and 9. Memory 72 of clinician programmer 22 may store software that causes processor 40 to generate different types of displays. In some examples, the clinician programmer 22 may optionally prompt the clinician or other user to select one or more types of patient event information to display (e.g., duration and severity of seizures or the event markers and corresponding time stamps), as well as the type of display format for displaying the event information. For example, the clinician may wish to view the event information as a bar graph showing number of activations of event indication button 58 per week for a three month period. As another example, the clinician may wish to view a table of all the event information provided by patient 14 organized based on the respective event markers.

FIGS. 7A-7E illustrate example user interfaces that may be presented by patient programmer 24 to allow a patient 14 to enter event information. Patient programmer 24 includes user input mechanisms 56a-56f (collectively "user input mechanisms 56"), event indication button 58, and display 60. Patient 14 may interact with user input mechanisms 56 to input event information into patient programmer 24, and, in some cases, control aspects of therapy delivered by IMD 16 within the limits programmed by a clinician. User input mechanisms include buttons 56a and 56b, which may be used to increase or decrease the therapy intensity, if allowed, and may perform other functions, as allowed by the operating software 54 (FIG. 3). An intensity of therapy may be modified by, for example, modifying a therapy parameter value, such as the current or voltage amplitude of stimulation signals, the frequency of stimulation signals, the shape of a stimulation signal or the electrode combination used to deliver the stimulation signal.

Multi-directional controller 56f may allow a user to navigate through menus displayed by display 60, and may include a button 56g that is actuated when the center of multi-directional controller 56f is pressed. Event indication button 58 is used to perform any of the functions ascribed to it herein, including, for example, generating an event marker and/or resetting or modifying a therapy cycle.

Display 60 may display graphical user interface screens that provide an interface for patient 14 to enter event information. While display 60 shows five individual screens in FIGS. 7A-7E, in other examples, the described screens may be displayed on a single screen divided into multiple sections, may be combined in any of other combinations of display screens, or may be omitted. The five screens shown in the illustrated examples include time stamp screen 122 (FIG. 7A), seizure type and severity screen 126 (FIG. 7B), duration screen 132 (FIG. 7C), notes screen 136 (FIG. 7D), and therapy efficacy screen 138 (FIG. 7E). Each screen presents patient 14 with event information associated with an event marker or allows patient 14 to enter event information.

Figure 7A:
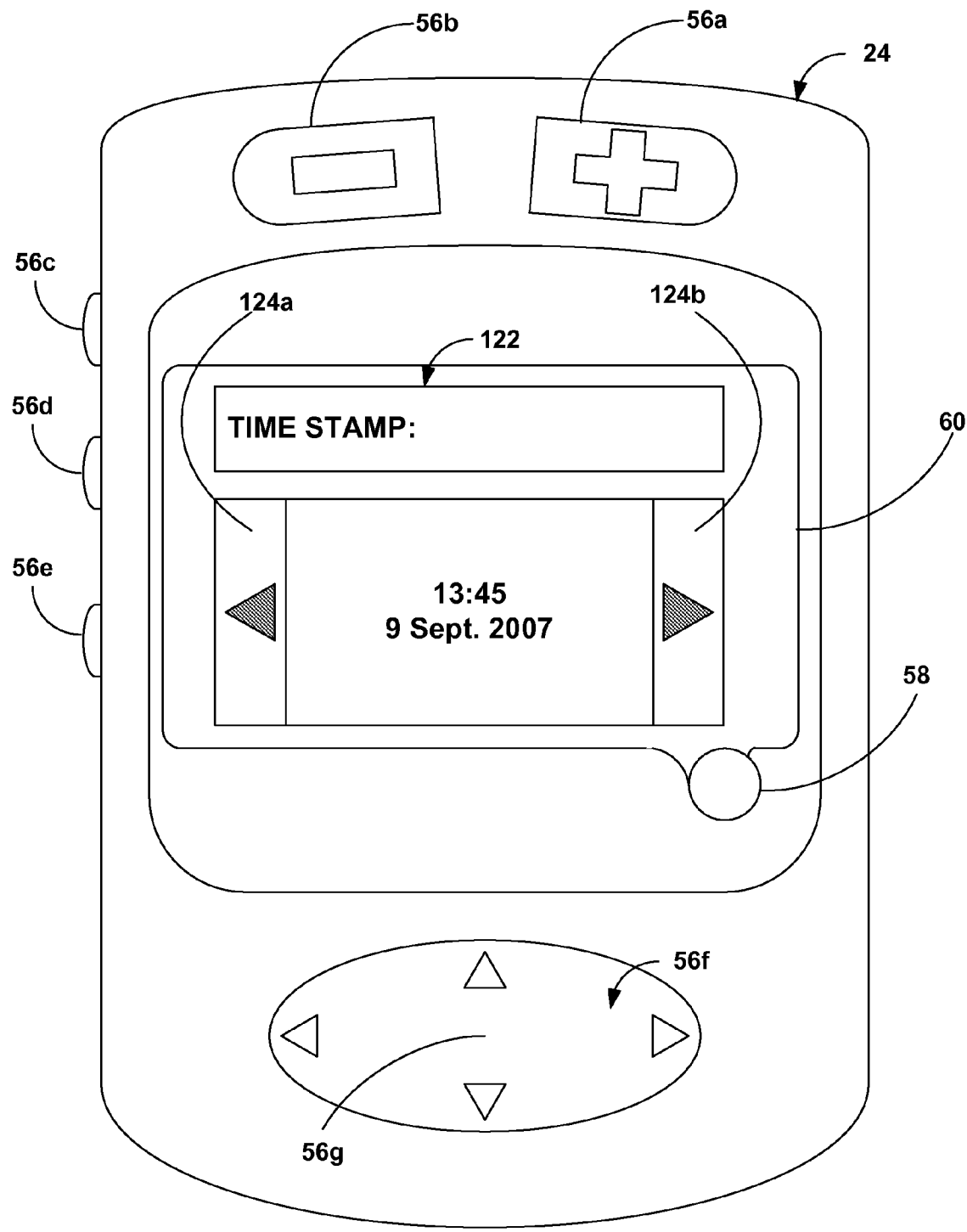
FIGS. 7A-7E illustrate example user interfaces that may be presented by a patient programmer.

Time stamp screen 122, illustrated in FIG. 7A, shows the time stamp of an event marker. In some examples, the patient 14 may change the time stamp displayed by selecting button 124*a* or 124*b* (either via a touch screen interface, or by controlling a cursor via user input mechanisms 56). Patient 14 may review (on screens such as those illustrated in FIGS. 7B-7E) event information associated with other event markers by changing the currently displayed time stamp. By selecting a stored time stamp, patient 14 is essentially selecting the event marker that was generated at the time reflected in the time stamp or otherwise associated with the time stamp (e.g., in some examples, patient 14 may modify the time stamp of an event marker). The other user interface screens 126, 132, 136, and 138 may display the respective information associated with the selected time stamp. In other examples, the time stamp may simply display the time stamp associated with the most recent activation of event indication button 58 and programmer 24 may not provide patient 14 with an option for reviewing event information associated with other event markers.

Figure 7B:
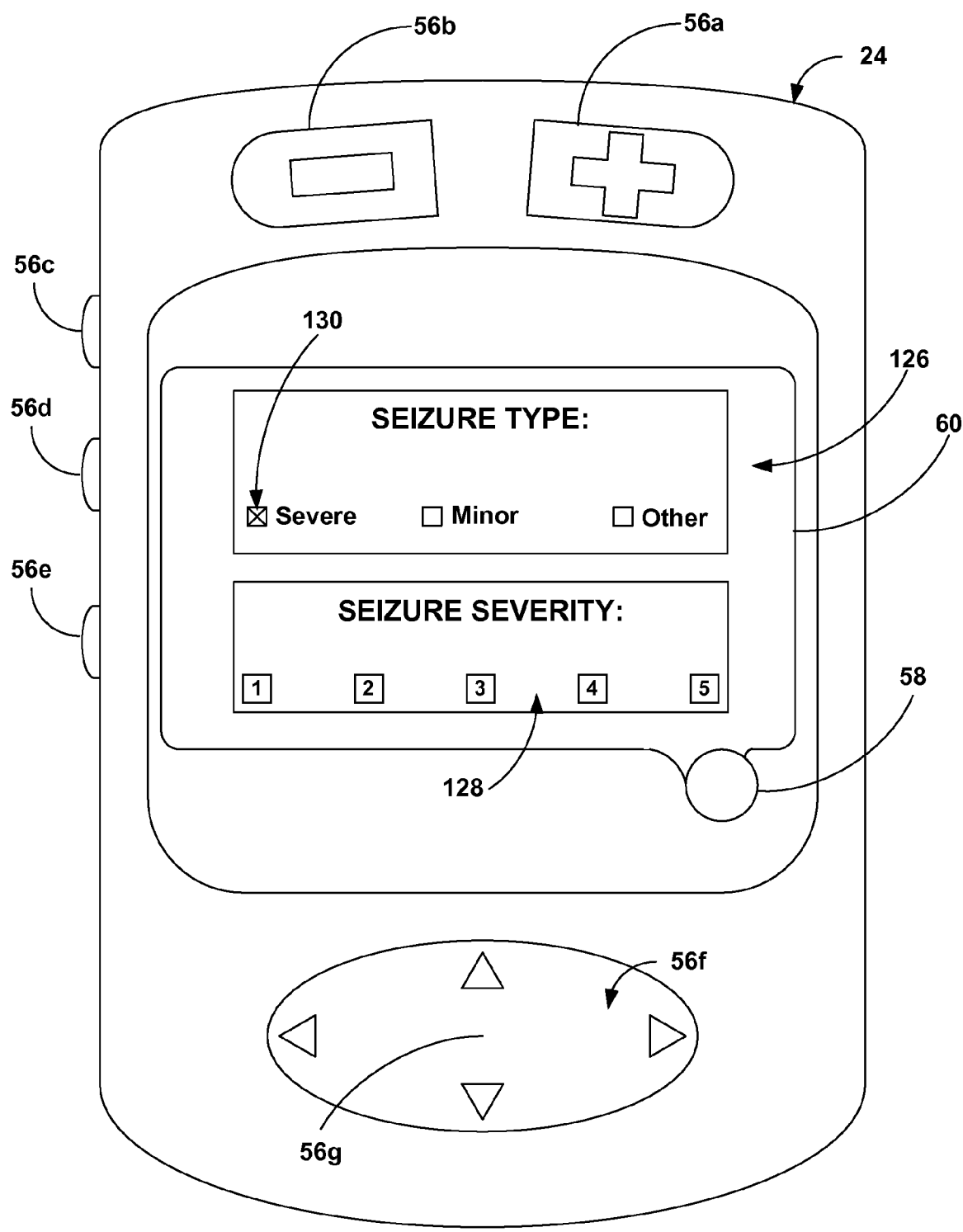

FIG. 7B shows seizure type and severity screen 126, which allows patient 14 to input information relating to the type of seizure experienced (if any) and the severity of the seizure. As described above, the clinician may assign nicknames to different seizure types that correspond to the name with which patient 14 refers to the seizure. In the illustrated example, "Severe" may refer to a tonic-clonic seizure and "Minor" may refer to an absence seizure. Patient 14 may select the type of seizure using multi-directional controller 56*f* or any other suitable element of user input mechanisms 56. Selection of a respective seizure type may be indicated by a selected box 130. In some examples, selecting "other" may prompt patient 14 to enter an alphanumeric description of the seizure type. In other examples, the seizure type may be selected from a dropdown menu (similar to the menu shown for duration screen 132), selected by an icon, and the like.

Patient 14 or another user may also input the severity of the seizure in severity subsection 128. The severity may be selected from a numeric list, as shown in FIG. 7B, where a rating of "1" represents least severe and a rating of "5" represents most severe, for example. In other examples, the severity may be selected from a textual list, or may be editable by patient 14. The severity may be correlated with the type of seizure indicated by the user. For example, a level 5 "Minor" seizure may be viewed by a clinician as less severe than a level 1 "Severe" seizure.

In some examples, however, the severity of the patient's seizure may be detected automatically based on values of one or more monitored physiological parameters of patient 14, such as an EEG signal or an ECG signal. As previously described, IMD 16 or another sensing device may monitor one or more physiological parameters of patient 14. The severity of the seizure may be determined based on, for example, the amplitude of the EEG signal waveform. Processor 40 of programmer 24 or a processor of another device (e.g., the sensing device or IMD 16) may determine the severity of the seizure and automatically record the severity within event information 50 of memory 42 of programmer 24. Severity may be categorized in terms of a graduated scale (e.g., a numerical scale) or another suitable scale. Alternatively, processor 42 may merely record the EEG signal and clinician or another computing device may determine the severity of the patient's seizure, if any, at the time the event marker was generated.

Figure 7C:
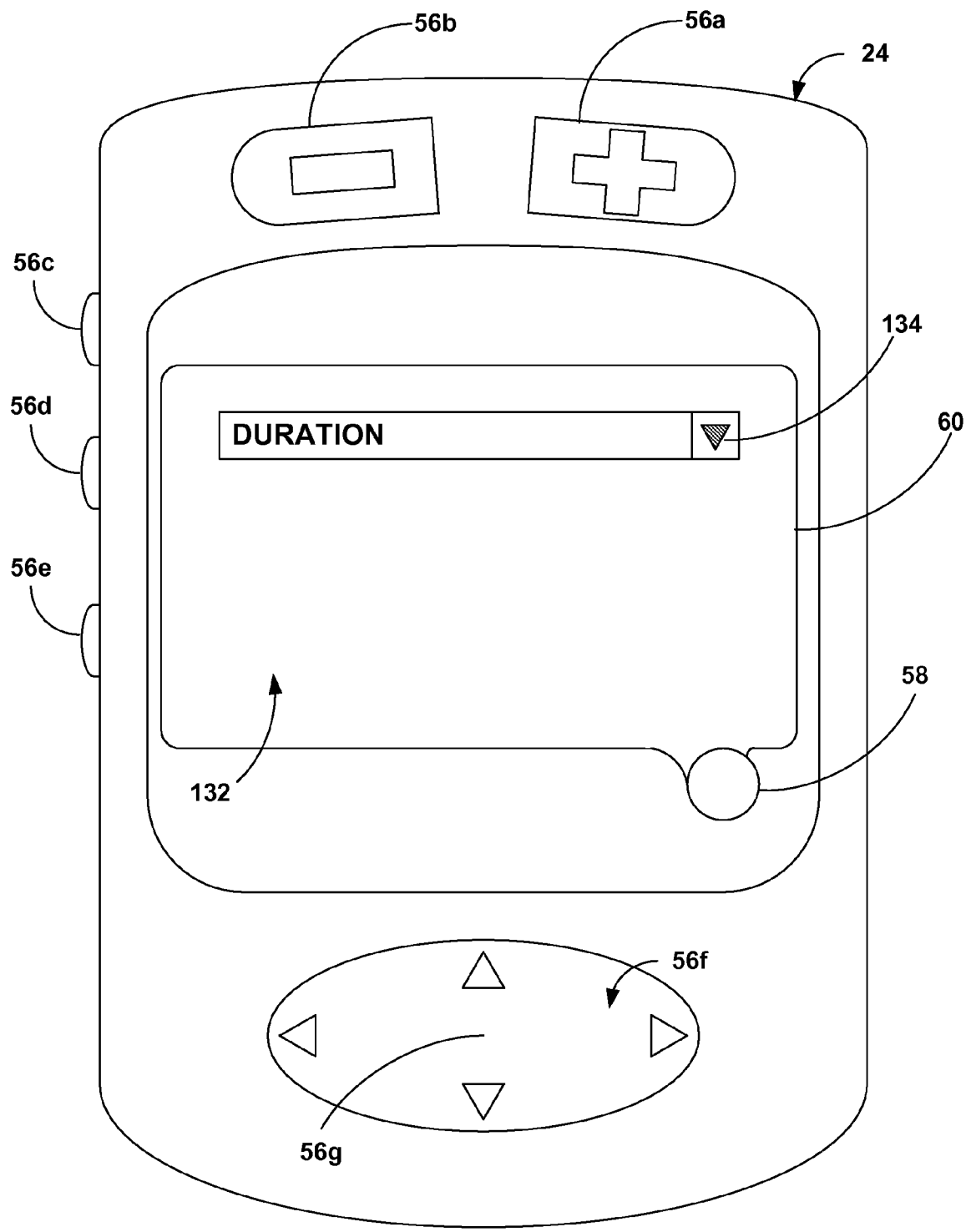

As illustrated in FIG. 7C, duration screen 132 allows a user, such as patient 14, to enter the duration of the seizure associated with the time stamp shown in screen 122 (i.e., a particular event marker). In some examples, the duration may initially be determined by processor 40. For example, patient 14 may activate event indication button 58 a first time when the patient event is sensed and a second time after patient 14 perceives the patient event as being complete. The time period between the first press of button 58 and second press of button 58 may be determined to be the duration of the event. In some examples, the duration may be edited at a later time by patient 14 or another user. In the illustrated example, the duration may be selected from dropdown menu 134. The dropdown menu may display durations in any desired increment, such as, for example, one minute, five minute or fifteen minute increments. In other examples, the seizure duration may be entered numerically, either through the use of an alphanumeric keypad, a touch screen, or a menu-driven interface.

Figure 7D:
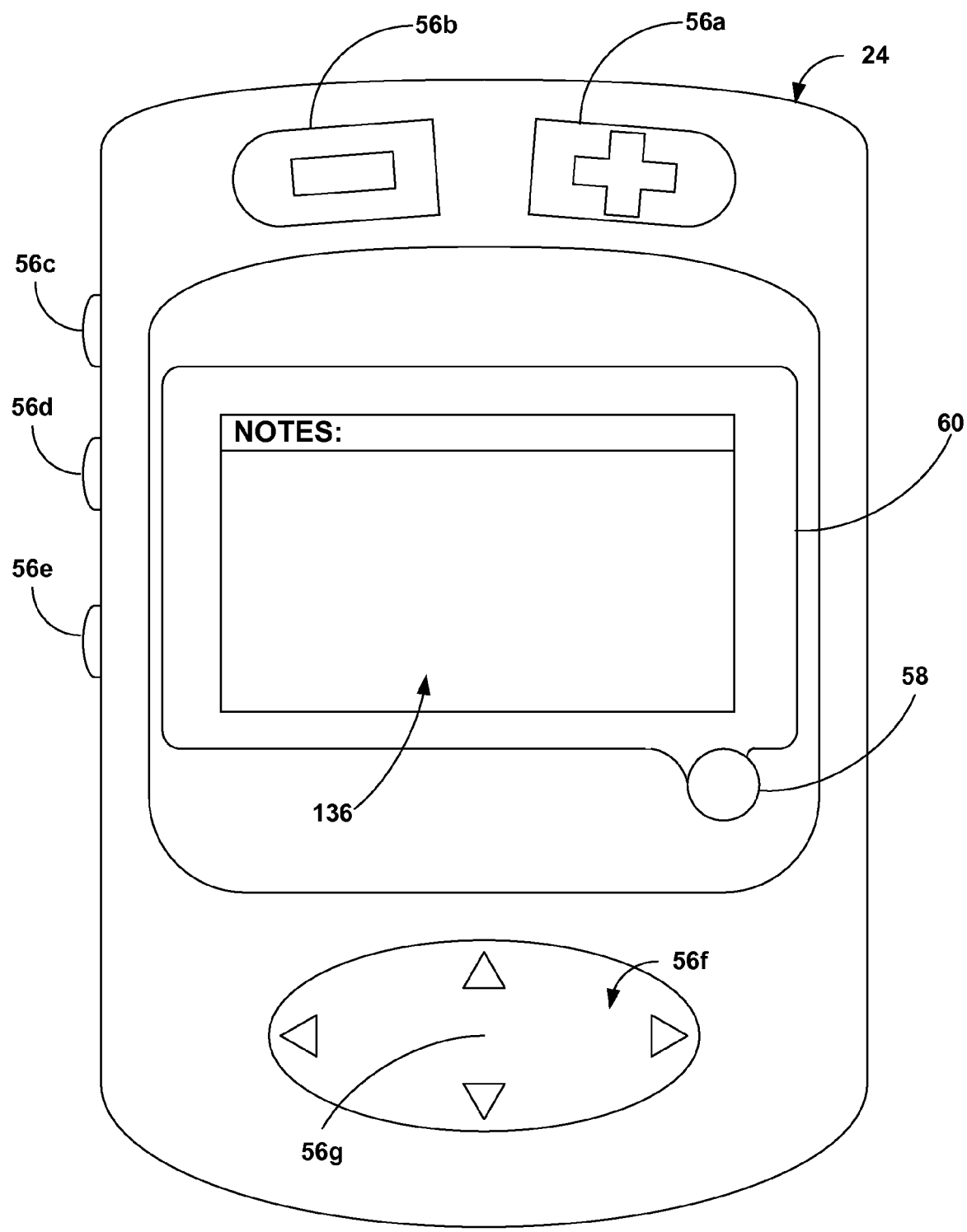
Figure 7E:
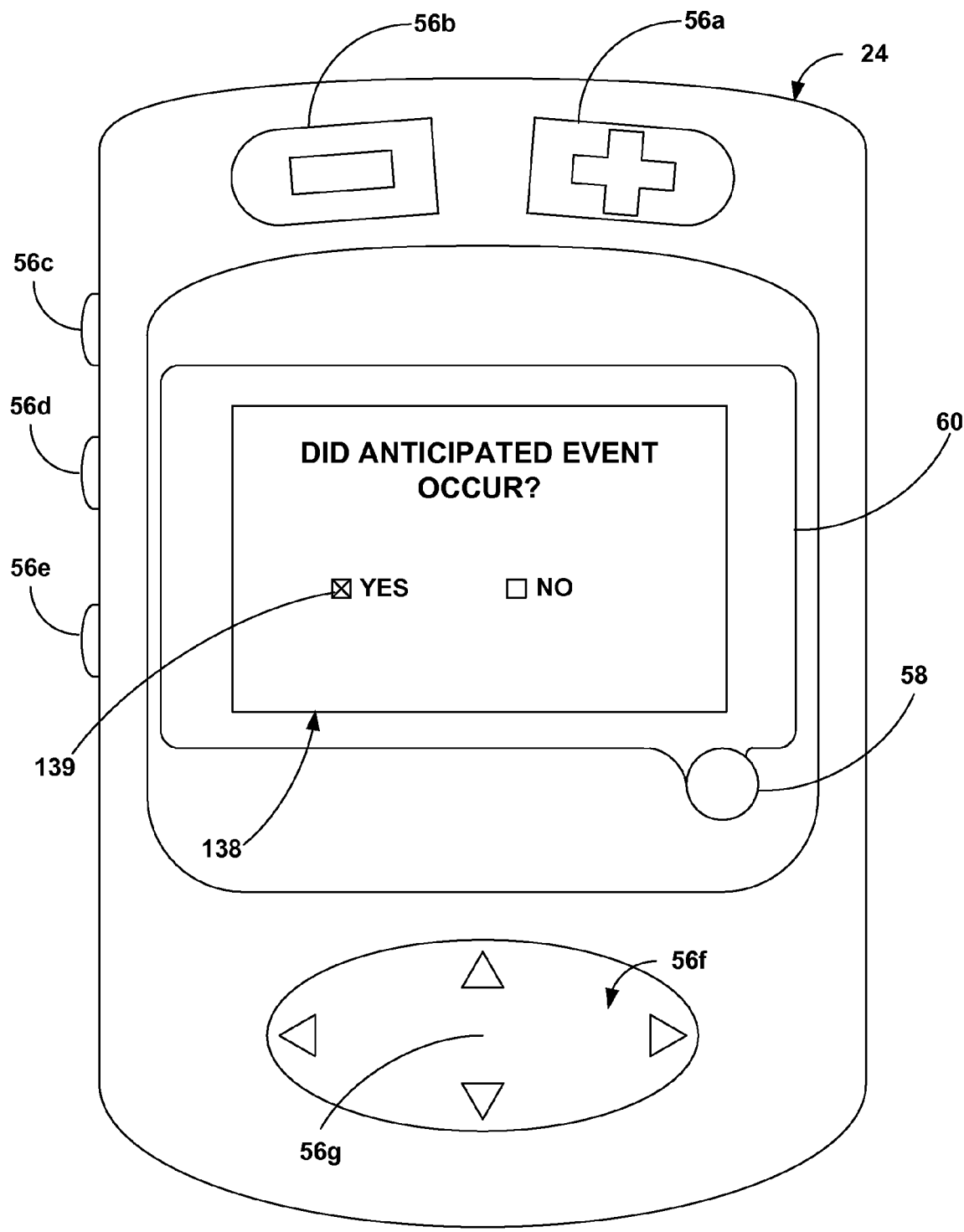

Notes section 136, shown in FIG. 7D, allows a user, such as patient 14, to enter any other notes deemed applicable to the therapy, event, or condition of patient 14. Information entered in the notes section 136 may include information regarding any of the other sections, such as seizure type and severity or duration, or may include notes about the current medication and dosage being taken by patient 24. For example, patient 14 may input notes regarding an activity being performed at the time of the event, a particular drug or drug dosage taken prior to or after the event, and the like.

As another example, illustrated in FIG. 7E, patient programmer 24 may present a therapy efficacy screen 138 that enables patient 14 to input information regarding the efficacy of therapy prior to, during or after the generation of the event marker. The therapy efficacy may relate to the duration, severity or type of seizure experienced by patient 14. For example, patient 14 may associate a sensed aura with a certain type or severity of seizure. If, after activating event indication button 58 and resetting the therapy cycle, the predicted seizure does not occur, patient 14 may infer that the therapy was efficacious. However, if the predicted seizure still occurs, patient 14 may infer that the therapy was not efficacious.

Therapy efficacy screen 138 may include, for example, one or more questions regarding the efficacy of therapy, which patient 14 may answer by, for example, selecting a box 139 with a predetermined answer. Questions posed via therapy efficacy screen 138 may include, for example: "Was the therapy effective?" "Did the anticipated event occur?" "Was therapy as effective as it was X days ago?" In other examples, a numerical scale or another type of graduated scale for assessing relative efficacy may be presented to patient 14 or patient 14 may provide another input indicative of efficacy.

Event information relating to the efficacy of therapy may be especially useful for evaluating therapy system 10 and determining the impact on a specific patient's therapy. While automatically detected physiological parameters are useful for evaluating therapy system 10, the subjective feedback from patient 14 may provide information not otherwise obtainable via the physiological parameter values. The clinician may consider the subjective feedback of patient 14 to be a valuable factor when determining whether to adjust the treatment plan for patient 14 or maintain the current plan, as well as for evaluating the condition of patient 14.

Efficacy of therapy may be a useful type of event information when processor 40 is configured to control IMD 16 (e.g., by generating a control signal that causes IMD 16 to perform some action) to adjust or modify therapy in response to receiving an indication of the occurrence of the event. As previously described, the therapy adjustments may include resetting a therapy cycle of stimulation or drug delivery, adjusting a therapy parameter value, such as increasing a concentration or size of a drug bolus or increasing intensity of stimulation (e.g., via increasing a current or voltage amplitude or signal frequency), or switching to another therapy program or group. The clinician may evaluate event information received from processor 40 of patient programmer 24, and, in some cases, other sources, such as IMD 16 or a sensing device, to evaluate the impact the therapy adjustment or modification on patient 14.

In other examples, patient programmer 24 may present other sections or user interface screens for receiving event information. For example, programmer 24 may present a drug entry screen that allows a patient 14 to enter drug information, such as the drug type and dose taken prior to the event. The drug entry screen may also allow patient 14 to enter the time when the drug was taken, or when a course of drugs began and ended. The drug information may be selected from, for example, a dropdown list, a selectable box, or a text entry. The drug entry screen may also allow patient 14 to enter other drugs taken after an event, such as a more potent anti-seizure medication taken to prevent more seizures for a time period after the initial event. In some examples, a clinician may assign shorter, recognizable names for the respective drugs taken by patient 14 to assist patient 14 from identifying and selecting the drug from a dropdown list or the like.

FIGS. 8A-8H illustrate various example user interfaces that may be presented by clinician programmer 22 to a user to display event information. The various user interface screens shown in FIGS. 8A-8H are merely exemplary, and other types of user interfaces are also contemplated.

Figure 8A:
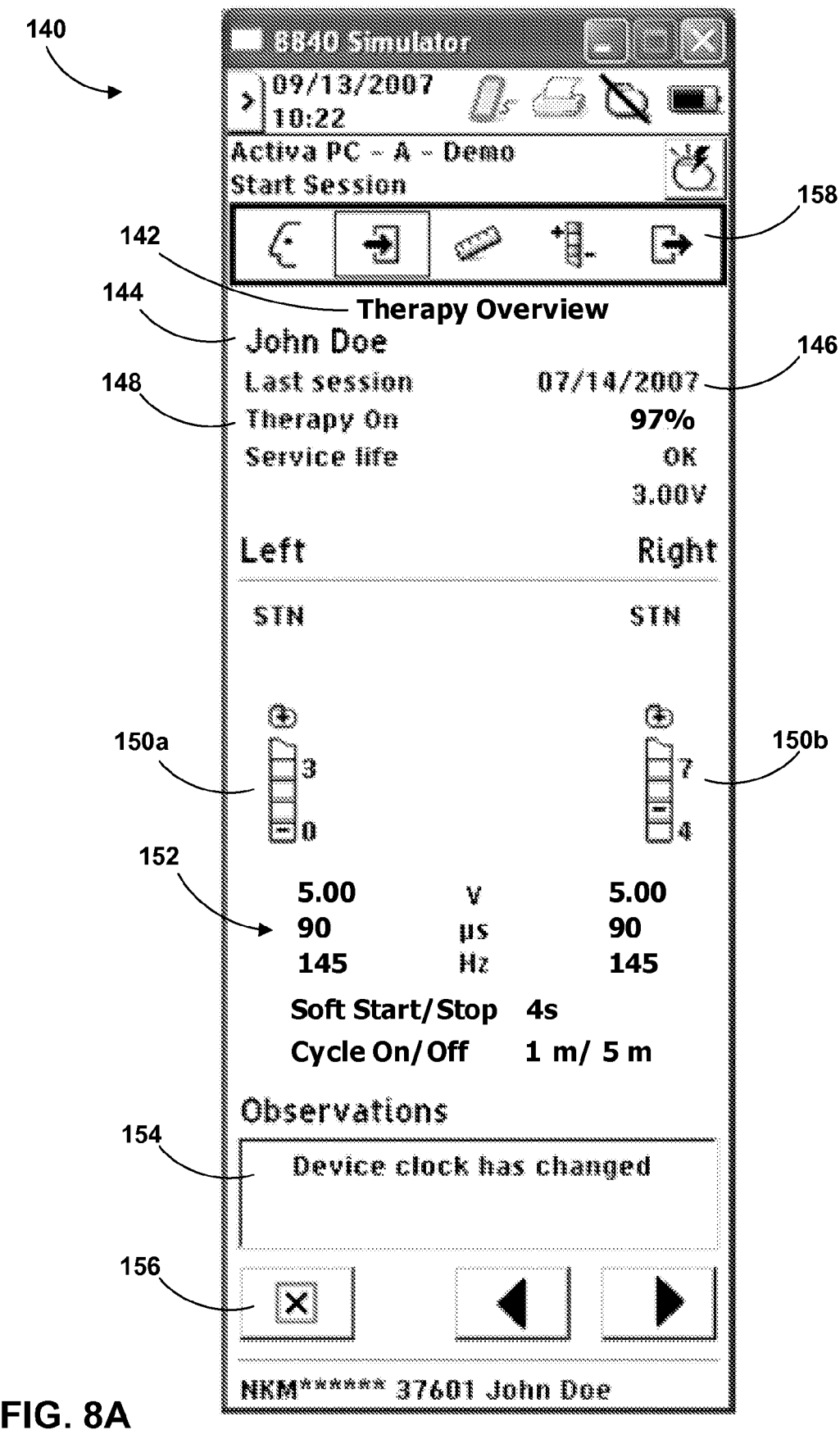

FIG. 8A shows an example user interface screen 140 that may be presented by clinician programmer 22 after the initial download of event information stored on patient programmer 24. Screen 140 includes a Therapy Overview 142 window that provides a summary of the stimulation parameter values that defined the stimulation therapy delivered by IMD 16 as well as other general information. In particular, Therapy Overview 142 presents the name 144 of patient 14, the date of the last communication session 146 between clinician programmer 22 and patient programmer 24 or IMD 16, and the amount of time that therapy was on 148 since the last session 146. Additionally, Therapy Overview 142 presents electrode configurations 150a and 150b for each of the two leads, respectively, and stimulation parameter value 152 including the pulse voltage, pulse width, pulse frequency and therapy cycle length. The electrode configuration and stimulation parameters may define a therapy program, which may also be associated into a group with one or more other therapy programs.

Therapy Overview 142 may also display any therapy observations 134, such as changes to patient programmer 24 or IMD 16, changes to the therapy program since last session, and the like. Processor 70 of clinician programmer 22 may be configured to interrogate IMD 16 and/or patient programmer 24 to ascertain whether certain changes, e.g., a change in the IMD 16 clock, have occurred since clinician programmer 22 last communicated with IMD 16 and/or patient programmer 24. Therapy Overview 142 may also include other information including, for example, the number of therapy programs stored on IMD 16, the clinician treating patient 14, and any other information pertinent to the therapy of patient 14.

Therapy Overview 142 (and all other user interface screens) may also include navigation icons 156, 158 that indicate a user, such as the clinician, may navigate between screens and select options such as print reports, exit, next, back, and the like. If the display of clinician programmer 22 is a touch screen display, the user may directly select the navigation icons 156, 158.

In other examples, Therapy Overview 142 may also indicate other information, including the implantation date of IMD 16 and the number of switches between therapy groups during the course of therapy delivery by IMD 16, if any, based on the number of event markers associated with a particular therapy group. Patient 14 may manually switch between therapy groups or the switch may automatically be made by IMD 16 or patient programmer 24 in response to activation of event indication button 58 of patient programmer 24.

As previously described, in some examples, processor 40 of patient programmer 24 or another computing device may determine whether a particular therapy group implemented by IMD 16 is effective based on the event markers associated with the therapy group. In one example, the number of event markers associated with the therapy program or group may be indicative of the efficacy of the respective program or group. In other examples, as described in U.S. patent application Ser. No. 12/236,316 to Giftakis et al., entitled, "PATIENT EVENT INDICATION" and filed on the same date as the present disclosure, processor 40 may calculate an event metric for a therapy program or group based on the one or more associated event markers and compare the event metric to a threshold value in order to determine whether the respective program or group provides efficacious therapy to patient 14. In some examples, the event metric may include a total number of event markers associated with the program or group, a number of event markers per unit of time associated with the program or group or a change from a baseline condition of patient 14 during the time the medical device delivered therapy with the particular therapy group. U.S. patent application Ser. No. 12/236,316 to Giftakis et al. is incorporated herein by reference in its entirety.

Figure 8B:
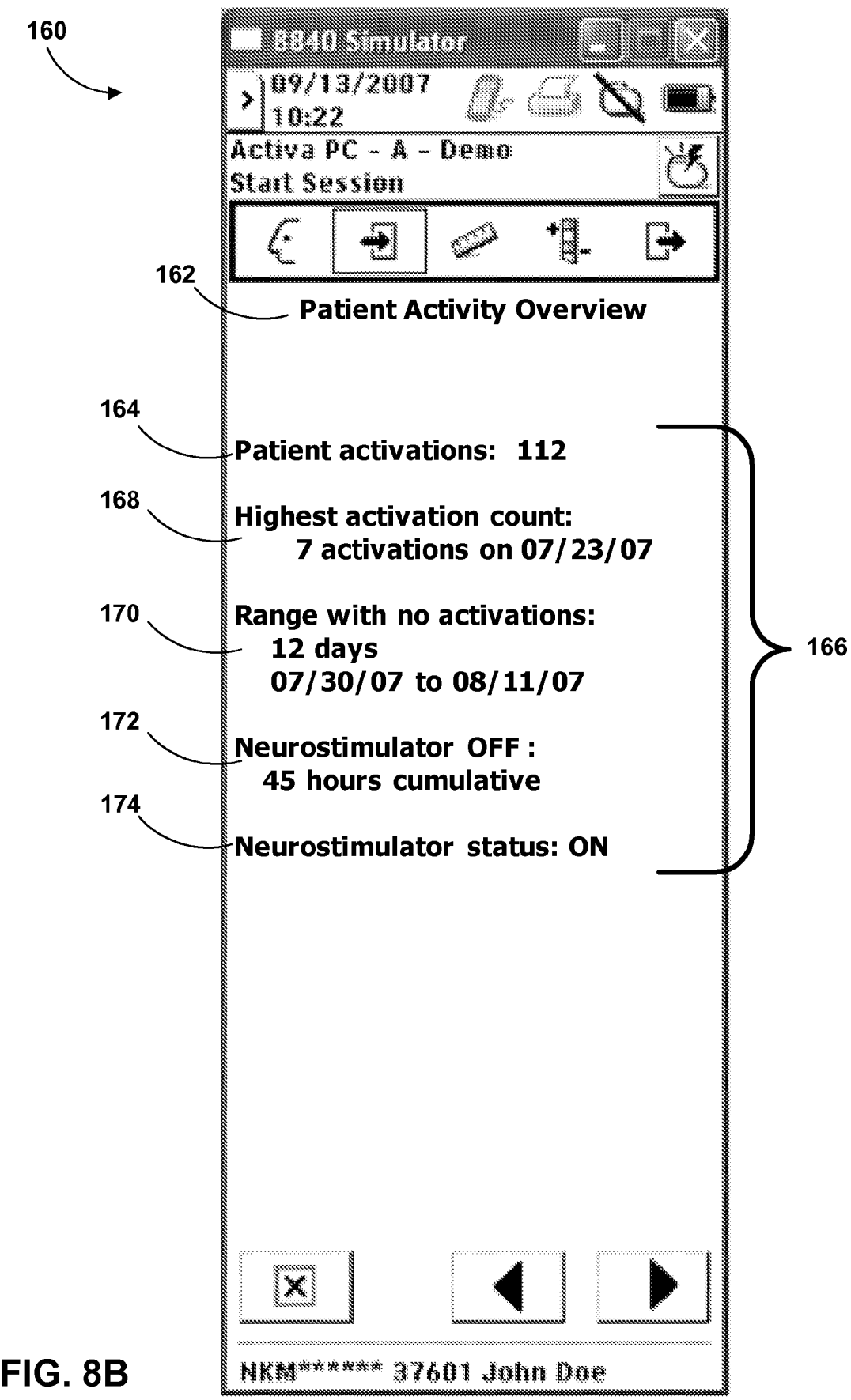

FIG. 8B illustrates another example user interface screen 160 that may be presented by clinician programmer 22. User interface screen 160 presents a Patient Activity Overview 162 window. Patient Activity Overview 162 may summarize the activities 166 performed by patient 14 since the last office visit. For example, activities 166 may include the total number of times 164 patient 14 activated event indication button 58 of patient programmer 24 during a certain period of time (e.g., the time since the patient's last clinician visit), the highest number of activations 168 of event indication button 58 in a given time period, such as one day, the longest time period between activations 170 of event indication button 58, the total amount of time that IMD 16 was turned off 172 by patient 14 during a certain period of time, and the current status 174 of IMD 16.

Figure 8C:
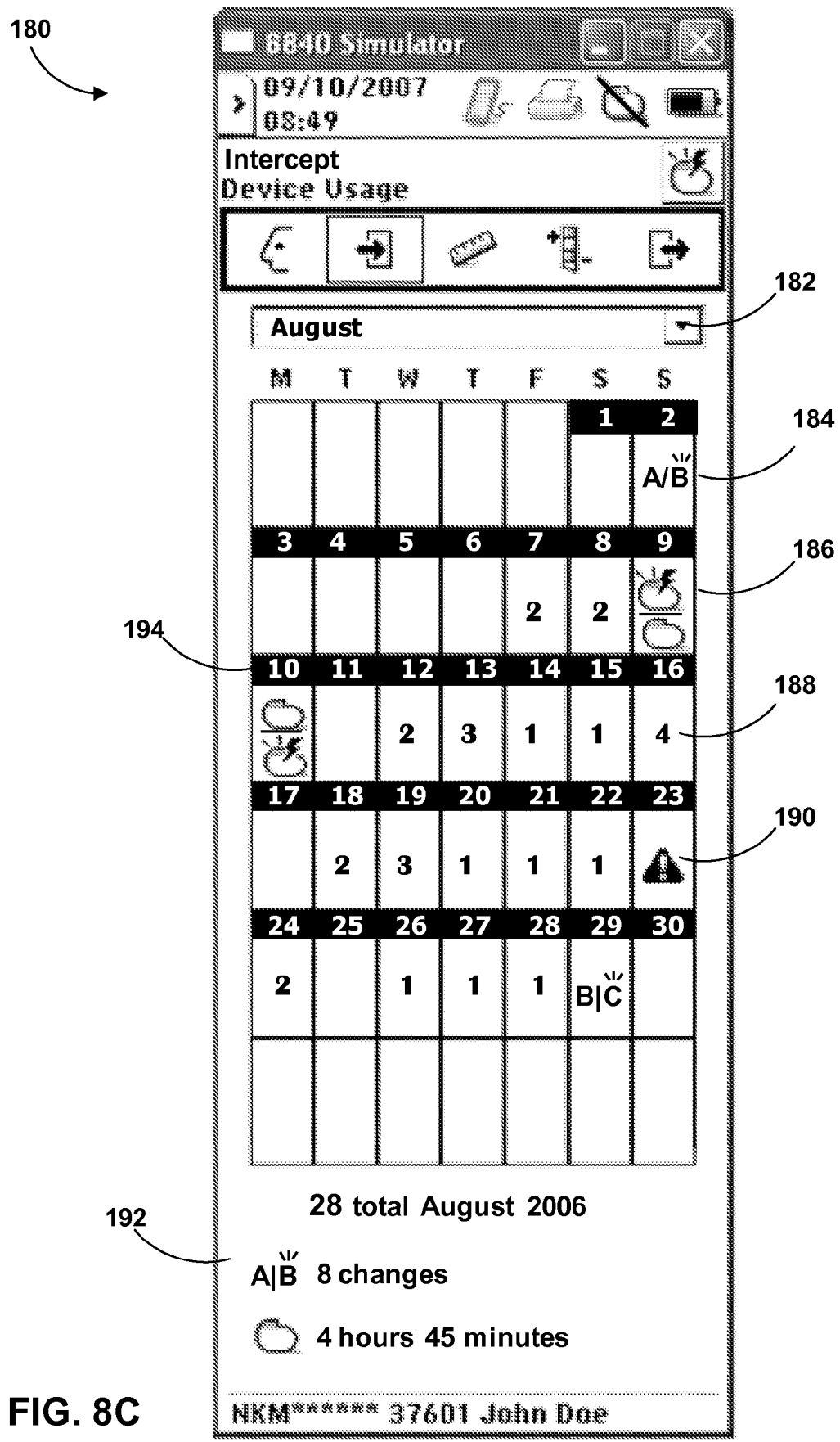

FIG. 8C illustrates another example user interface screen 180 that may be presented to a clinician by clinician programmer 22. User interface screen 180 presents a calendar view of the patient event information. Dropdown box 182 allows the clinician to select the desired time window to view. In the example shown in FIG. 8C, the time window is on the order of one month. However, other time windows are contemplated, such as days, weeks or more than one month. In the example shown in FIG. 8C, the month selected for viewing by the user may be shown in a calendar view, with the dates 194 of the month located at the tops of respective boxes. The location, color, and text of the dates and other displayed information is for illustrative purposes only, and is to be understood to be non-limiting. Each day may indicate event information, or the lack thereof, through the use of multiple elements. For example, in the illustrated example, the number of activations of event indication button 58, i.e., the number of event markers, is indicated for each day by a simple numeral 188 in approximately the center of the box corresponding to the day. A clinician may select a particular day and review the time stamp for each event marker.

When IMD 16 is able to provide therapy according to different therapy programs, an indication 184 of the date when the therapy program implemented by IMD 16 was changed may be given in symbolic form, as illustrated, or may be presented in textual form. Additionally, an indication 190 that more than one seizure actually occurred on a single day may be provided in symbolic or text form. The actual seizure detection may be based on physiological parameter data and/or input from patient 14. An indication 186 that stimulation was turned on or off, e.g., by patient 14 either purposefully or inadvertently, may also be provided in the calendar view.

The calendar view may also provide a summary 192 of the information presented. For example, in the illustrated example, the summary 192 includes the total number of activations of event indication button 58 in the month of August, the number of therapy program mode changes in the month of August, and the total time the therapy device was in an off state. A user may select the month or other time frame displayed via dropdown box 182, in which case summary 192 may provide the event information relevant to the selected time frame. In other examples, other summary data may be provided by calendar view 180, such as, for example, the number of each type of seizure, the average number of seizures per amount of time, a summary of event information from a previous time period to enable comparison between more than one time period, a rating from patient 14 as to the efficacy of therapy and the like.

Clinician programmer 22 may also permit the clinician to program patient programmer 24, configure IMD 16, and perform tests on IMD 16. In one example, a clinician may use clinician programmer 22 to program patient programmer 24 and IMD 16 to operate in a placebo mode. In some cases, a clinician may wish to evaluate whether patient programmer 24 including an event indication button 58 that allows patient 14 some control over therapy delivery by IMD 16 is a useful feature. As previously described, activation of event indication button 58 by patient 14 may result in a shift between therapy programs or program groups implemented by IMD 16 or a change in a therapy cycle. A therapy cycle may include at least one "on-cycle," during which stimulation is turned on, and at least one "off cycle," during which stimulation is not delivered to patient 14. During the "on-cycle," stimulation may be turned on and, off, for example, if stimulation is provided as pulses or bursts of pulses.

Patient 14 may test patient programmer 24 during a trial stage, which may be, for example, a few days, weeks, months or any other time period that provides sufficient time to evaluate patient programmer 24 in view of any fluctuations in the patient's condition. The clinician may determine whether to implement patient programmer 24 or another patient programmer that does not include the functionality of event indication button 58 (e.g., a modified patient programmer 24) based on the frequency of usage of indication button 58 by patient 14 and feedback indicating the efficacy of indication button 58.

In the placebo mode, processor 40 of patient programmer 24 may generate a placebo indication to patient 14 each time event indication button 58 is activated. Processor 40, however, does not implement control of IMD 16 or otherwise take action to modify therapy delivered by IMD 16. The placebo indication may be presented, e.g., via display 60 of patient programmer 24, via an audible sound generated by patient programmer 24 or another sensory cue. The placebo indication provides feedback to patient 14 to indicate that the activation of event indication button 58 was received, and in some cases, may even indicate that the therapy delivered by IMD 16 was adjusted in response to the activation of event indication button 58.

The clinician may not inform patient 14 that event indication button 58 is merely a placebo and does not directly affect IMD 16. Thus, patient 14 may believe that therapy was triggered, a therapy cycle was restarted or therapy was otherwise modified after event indication button 58 was activated. In some cases, receiving the placebo indication may cause the placebo effect, in which patient 14 feels therapeutic effects, although IMD 16 functionality was not changed. During this trial stage, IMD 16 may be set to deliver stimulation at regular intervals, substantially continuously or deliver no stimulation at all. If a clinician may wish to evaluate whether patient 14 requires therapy in order to control a condition, such as seizures, IMD 16 may be configured to withhold stimulation during the trial stage.

The clinician may determine whether to implement the patient programmer 24 including a functional event indication button 58 based on the frequency of usage of the event indication button 58 by patient 14 and feedback indicating the efficacy of the event indication button 58 during the trial stage. The clinician may evaluate whether patient 14 believed event indication button 58 had any effect on therapy based on the patient feedback reflected in the event information. If the patient feedback indicated that activating event indication button 58 provided efficacious therapy when event indication button 58 merely resulted in the placebo indication, the clinician may discern that patient 14 does not need patient programmer 24 that includes a functional event indication button 58. On the other hand, if the feedback from patient 14 indicated that activating event indication button 58 did not provide efficacious therapy, the clinician may wish to provide patient 14 with a patient programmer 24 that includes a functioning event indication button 58 that allows patient 14 to better control therapy delivery by IMD 16.

Figure 8D:
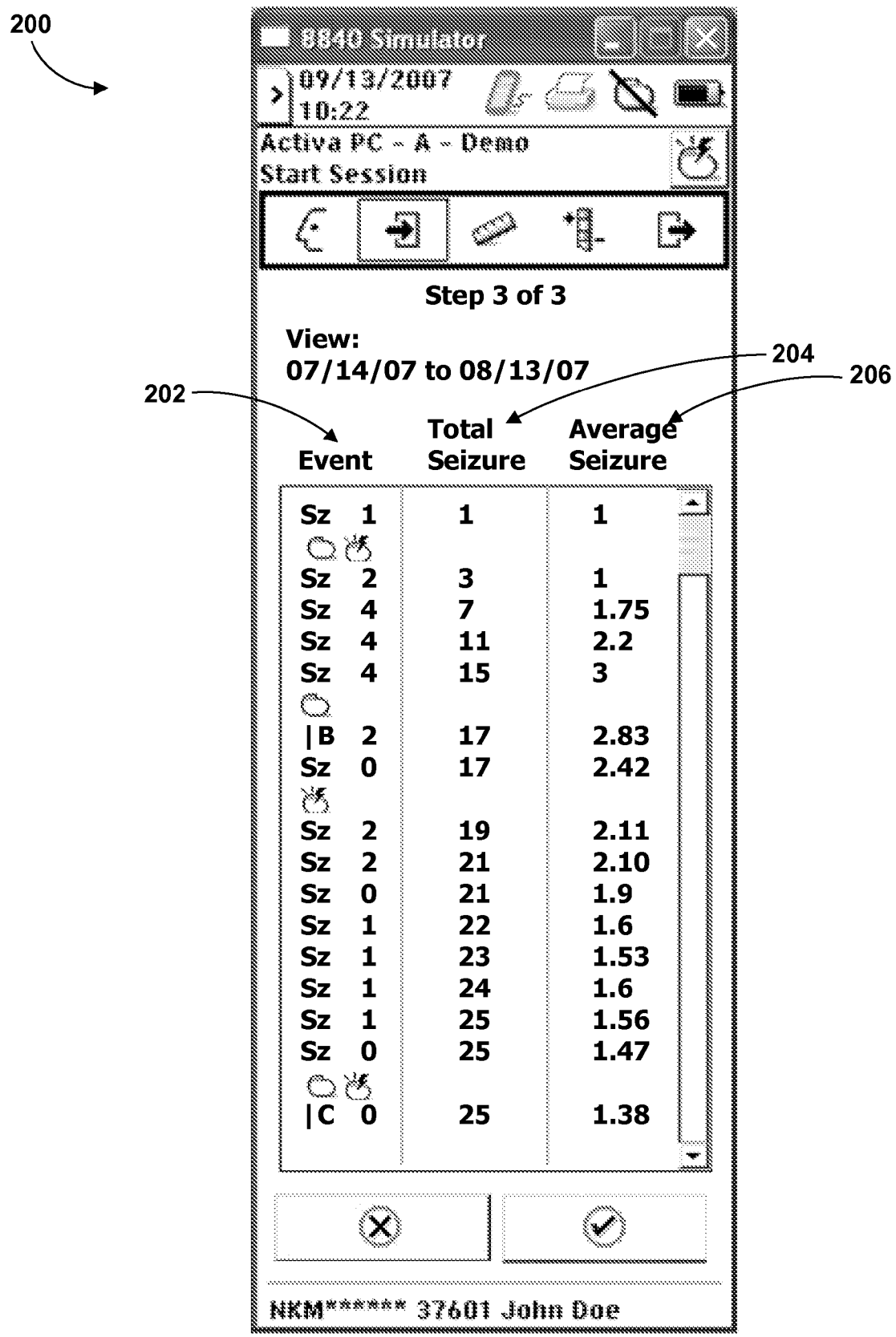

FIG. 8D illustrates another example user interface screen 200 clinician programmer 22 may present to a user. User interface screen 200 illustrates a tabular arrangement of patient event information for the period of a month, where each row includes information from one day. Column 202 displays the number of events per day and other ancillary information including, for example, days when the therapy was turned off, turned on, or modified. Column 204 displays a cumulative total of the number of events for the displayed period, and column 206 displays a cumulative average of events per day over the time period displayed. In some cases, the average number of event markers per day may provide more meaningful information to a clinician when determining whether therapy system 10 is providing effective therapy to patient 14.

Although a time period of a month is shown in FIG. 8D, in other examples, user interface screen 200 may display any suitable time period, such as one week, two weeks, three weeks or more than a month.

Figure 8E:
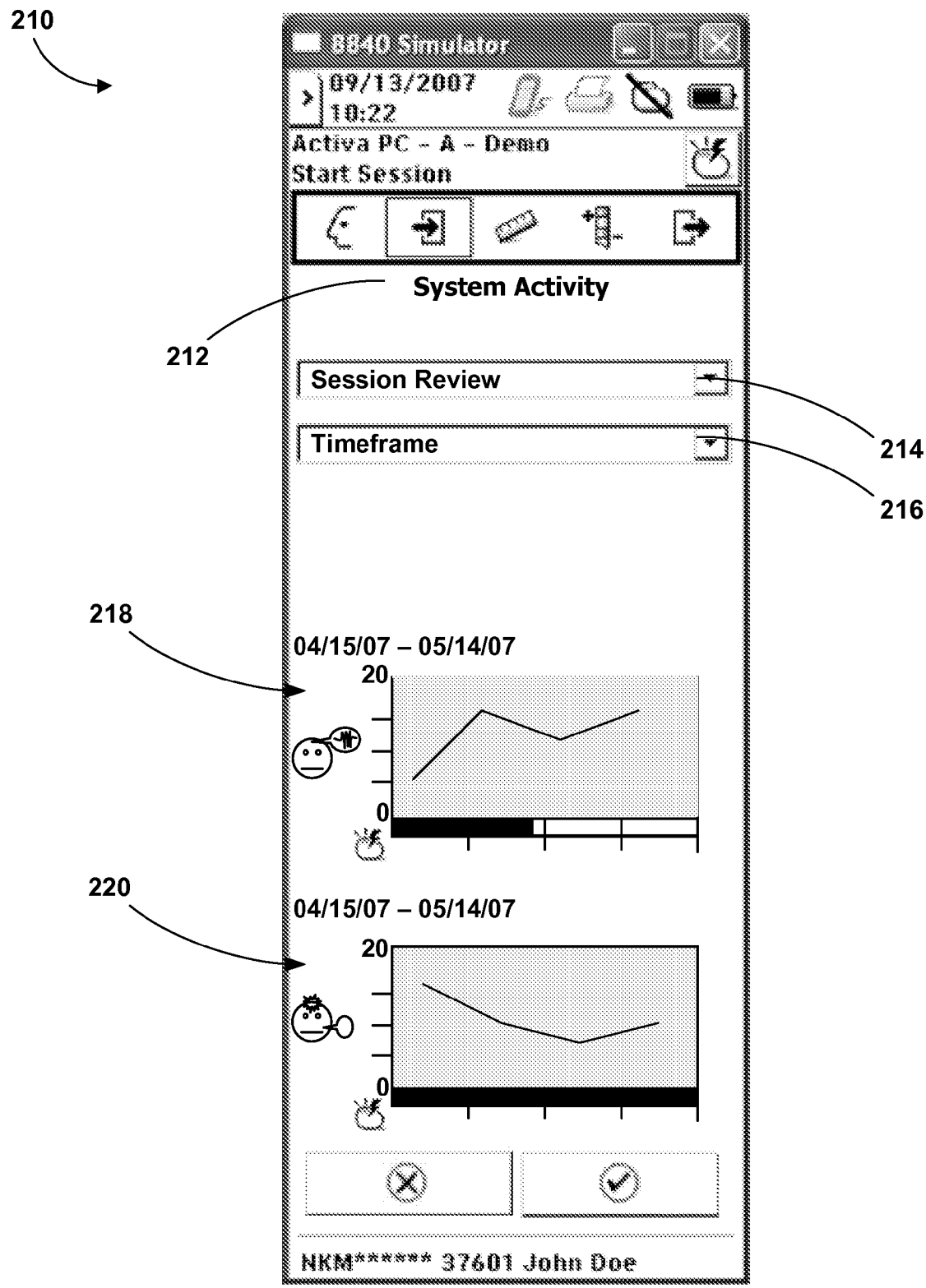

FIG. 8E shows yet another example user interface screen 210 clinician programmer 22 may present to a user. System Activity 212 window illustrates a first dropdown box 214 and a second dropdown box 216 for selecting the type of information displayed and the timeframe displayed, respectively. The illustrated example shows the number of events per unit time in graphical form, but any other type of patient event information described herein may be displayed in any suitable format described herein.

User interface screen 210 may be useful for displaying event information for a large range of time. For example, the x-axis of each of graphs 218 and 220 may represent time (e.g., measured in days, weeks or months), while the y-axis represents the number of event markers, which may be indicative of the number of seizures. Alternatively, processor 40 of clinician programmer 22 may discern the actual number of seizure occurrences based on patient feedback and the y-axis may represent the number of seizures.

Figure 8F:
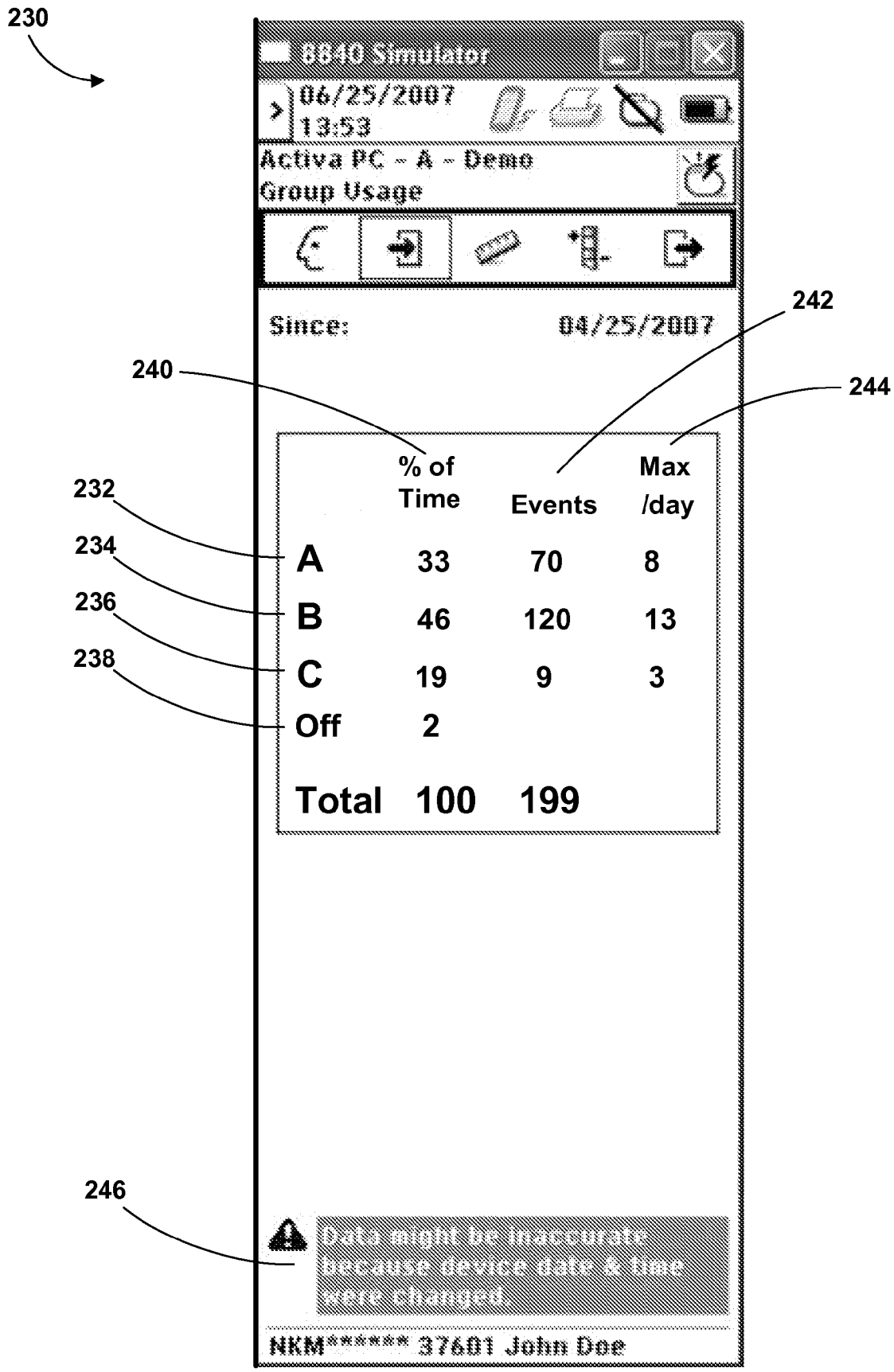

FIG. 8F illustrates another example user interface screen 230 that may be presented to a clinician by clinician programmer 22. Screen 230 presents a table of selected event information for each of three therapy programs: program A 232, program B 234 and program C 236, and an off setting 238 of IMD 16. In other examples, each row may indicate a therapy program group instead of a therapy program. Column 240 lists the percentage of time IMD 16 spent in each therapy program, e.g., during a time period selected by a user, column 242 lists the number of event markers that are associated with each therapy program, and column 244 lists the maximum number of event markers that were generated in one day while IMD 16 was delivering therapy in accordance with the respective therapy program. Screen 230 may also show a warning 246 indicating that data may be inaccurate because the date and time set in IMD 16 have been changed.

Figure 8G:
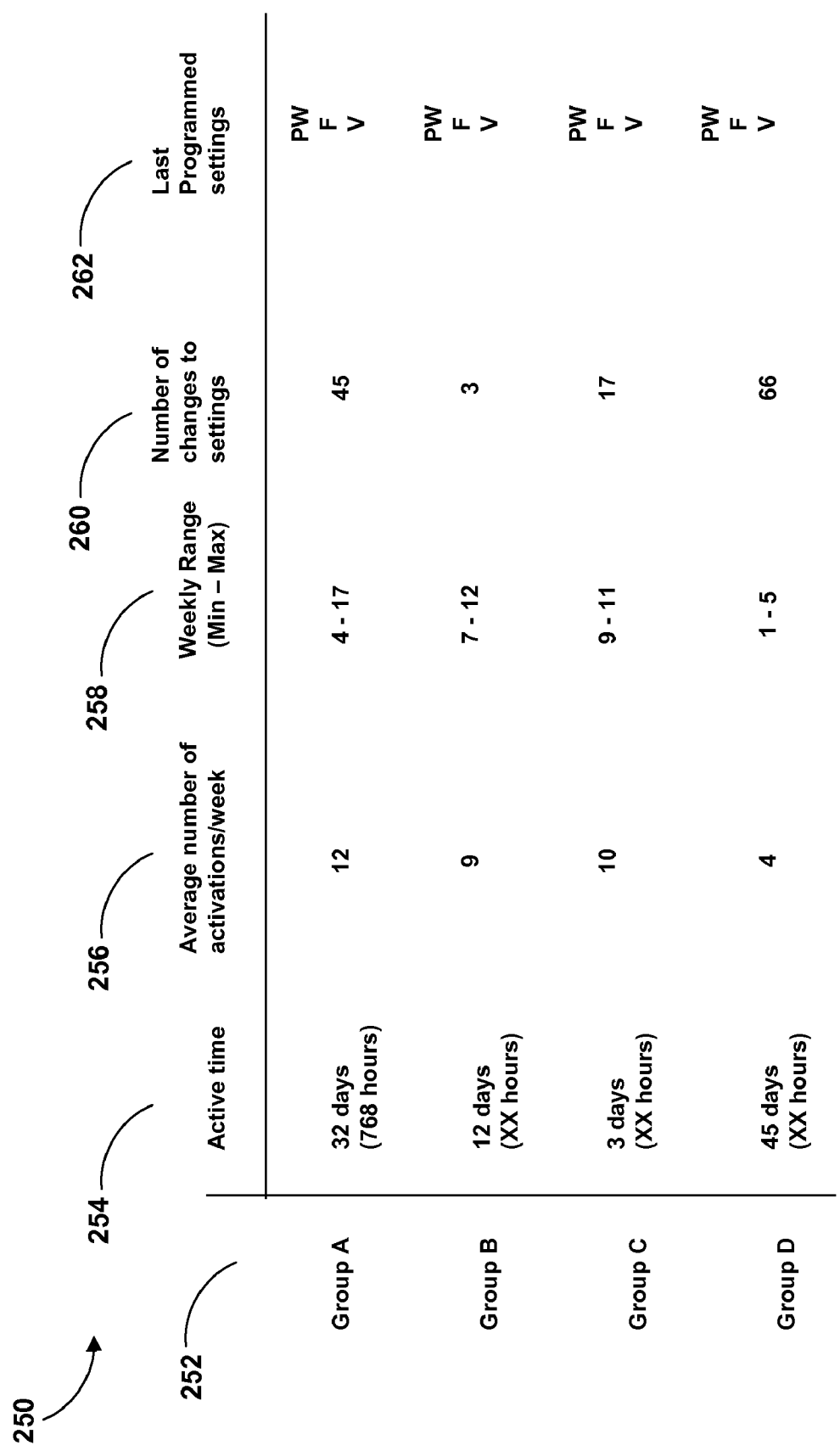

FIG. 8G illustrates a table 250 of event information that may be generated and presented by clinician programmer 22. The therapy program groups are listed in column 252. The amount of time that IMD 16 delivered therapy in accordance with each therapy group (i.e., the "active time") during a time period selected by a user or in the time period since the last interaction between clinician programmer 22 and patient programmer 24 may be provided in column 254 in both days and hours. The average number of activations of the particular therapy group per week may be listed in column 256, the minimum and maximum number of activations per week of the particular therapy group may be listed in column 258, the number of changes to therapy program settings (e.g., therapy parameter values) may be listed in column 260, and the last programmed settings, including the pulse width, frequency, and voltage may be listed in column 262. Again, the particular event information shown in FIG. 8G is one example, and any of the event information described herein may be added, substituted or removed from the table in FIG. 8G. Additionally, the event information may be grouped differently than shown in FIG. 8G, and may be grouped in any manner desired by the clinician or other user. The clinician may annotate the data displayed in FIG. 8G with any comments provided by patient 14 or any observations made by the clinician. Clinician programmer 22 may allow the clinician to enter typed or written notes, or may accept oral notes. Other illustrated user interface screens may also allow a clinician to annotate the data or screens presented.

The table of event information shown in FIG. 8G may be useful for evaluating which therapy groups provided the most effective therapy to patient 14 relative to the other therapy groups. If patient programmer 24 is set such that patient 14 has the freedom to select the program group, the table of event information shown in FIG. 8G may also be useful for determining which program group patient 14 preferred (e.g., based on the active time for each program group). The clinician may take this information into consideration when selecting a chronic therapy group for patient 14 or for generating additional therapy program groups to trial on patient 14.

FIG. 8H shows an exemplary table 270 similar to FIG. 8G. However, FIG. 8H shows event information from the current session 272, the previous session 274, and two sessions ago 276. The information listed for each session is similar to that described in FIG. 8G, and again, may include any of the event information described herein.

Other user interface screens are also contemplated. For example, clinician programmer 22 may present a user interface that allows a clinician to modify the therapy parameter values stored within IMD 16 or patient programmer 24. As another example, clinician programmer 22 may present a user interface that allows a clinician to make changes to the operating software used by patient programmer 24. Still other user interface screens may allow a clinician to modify the lists presented to patient 14 by user interface 44 of patient programmer 24. For example, the clinician may add, delete or modify the type of event information patient 14 may provide via user interface 44 of patient programmer 24, or the presentation for receiving the event information.

FIGS. 9A-9G illustrate example data formats (e.g., graphs and tables) that processor 70 of clinician programmer 22 or a processor of another device may generate and present in order to display event information to a user. While the description of FIGS. 9A-9G primarily refers to clinician programmer 22, in other examples, another computing device may generate the data formats and displays described herein. Displaying patient event information in graphic or tabular form may allow a user, such as a clinician, to more easily identify subtle or significant trends in the event information, or identify any relationships between occurrences of different types of information. Thus, clinician programmer 22 may store the necessary software, firmware, hardware or combinations thereof to generate one or more types of graphical or tabular displays.

Figure 9A:
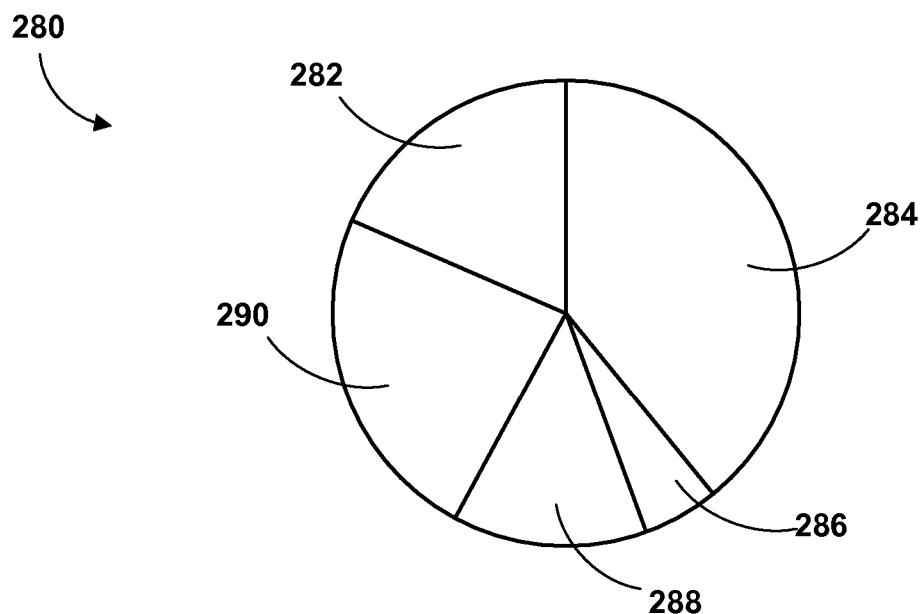

FIG. 9A illustrates a pie chart 280. In this example, pie chart 280 represents the number of events associated with five different types of medications or combination of medications during a particular time period, which the user may specify or which clinician programmer 22 may automatically select. In other examples, pie chart 280 may represent the number of events associated with different therapy programs or program groups (e.g., stimulation programs). For example, slice 282 may indicate that eighteen event markers were generated (i.e., patient 14 activated event indication button 58 18 times) while patient 14 was ingesting medication A or was otherwise under the influence of medication A (e.g., a fluid delivery device may automatically deliver medication A to patient 14 or deliver medication A to patient 14 at the direction of patient 14). Slice 284 of pie chart 280 may indicate that thirty-eight event markers were generated while patient 14 was ingesting medication A or otherwise under the influence of medical A. Similarly, slice 286 may represent the total number of event markers associated with medication C, slice 288 may represent the total number of event markers associated with medication D, and slice 190 may represent the total number of event markers associated with medication E.

Pie chart 280 may facilitate the clear and concise presentation of certain types of information, and may enable a clinician to quickly determine the relative effectiveness of a medication. Furthermore, in some examples, pie chart 180 may be interactive. A user may select one slice 282, 284, 286, 288, and 290 in order to ascertain more information about the event markers associated with the slice. For example, if pie chart 280 is presented on a display 60 of clinician programmer 22, the user may select one slice of pie chart 280 with a peripheral pointing device (e.g., a mouse or a stylet). In response, processor 70 of clinician programmer 24 may generate another display that presents the requested information, such as the date stamp for the event markers associated with the selected slice of pie chart 280, as well as event information (e.g., patient feedback) associated with the event markers (e.g., type of seizure, severity of seizure, and/or duration of seizure).

Although FIG. 9A is directed to a number of events per drug use, other types of information may be advantageously displayed as pie charts. For example, the relative number of events per therapy program or program group, the relative number of seizures per time of day or other time period, and the like may be easily displayed and ascertained via pie charts.

Figure 9B:
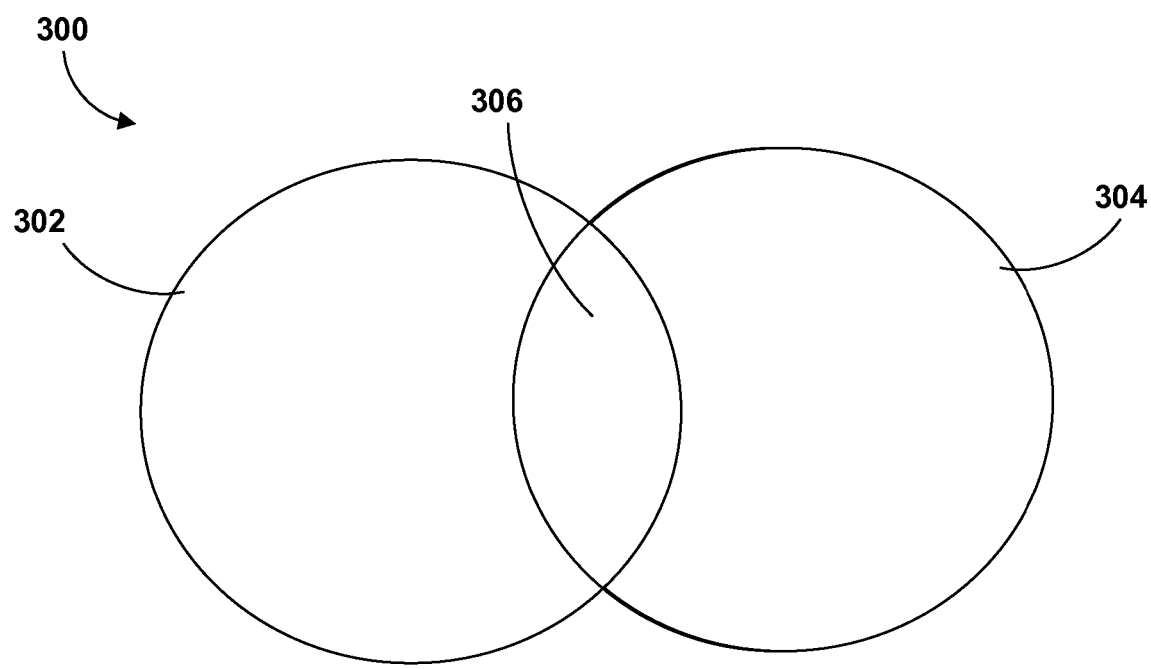

FIG. 9B illustrates an example of a Venn diagram 300 that may be useful for representing event information. In the example shown in FIG. 9B, circle 302 represents the number of times patient 14 activated event indication button 58 of patient programmer 24 and reset a therapy cycle, and circle 304 represents the number of times a certain type of seizure, such as a tonic-clonic seizure, was experienced by patient 14. Section 306 between circle 302 and circle 304 represents the number of times the patient 14 activated the event indication button 58 and the event resulted in the selected type of seizure. A clinician may view a Venn diagram 300 and quickly ascertain the effectiveness of a therapy, e.g., based on the relative size of the overlapping section 306 or the patient event indication button 58 activations associated with section 306. In the example shown in FIG. 9B, a larger overlapping section 306 may represent a less effective therapy. Once again, other types of event information may be displayed in a Venn diagram 300, and the desired data may be indicated by the clinician using user interface 74 of clinician programmer 22.

Examples of Venn diagrams for display of patient data, such as event information, as well as other types of useful displays of information are described in commonly-assigned U.S. patent application Ser. No. 11/789,690, entitled, 'GRAPHICAL DISPLAY OF PATIENT DATA," which is incorporated herein by reference in its entirety. As described in U.S. patent application Ser. No. 11/789,690, each section of Venn diagram 300 (e.g., circles 302, 304, overlapping section 306 and the portions of circles 302, 304 that do not overlap) may provide a dynamic link. The clinician may select one or more portions of Venn diagram 300 in order to access more detailed information about the event information associated with the selected section of Venn diagram 300.

Figure 9C:
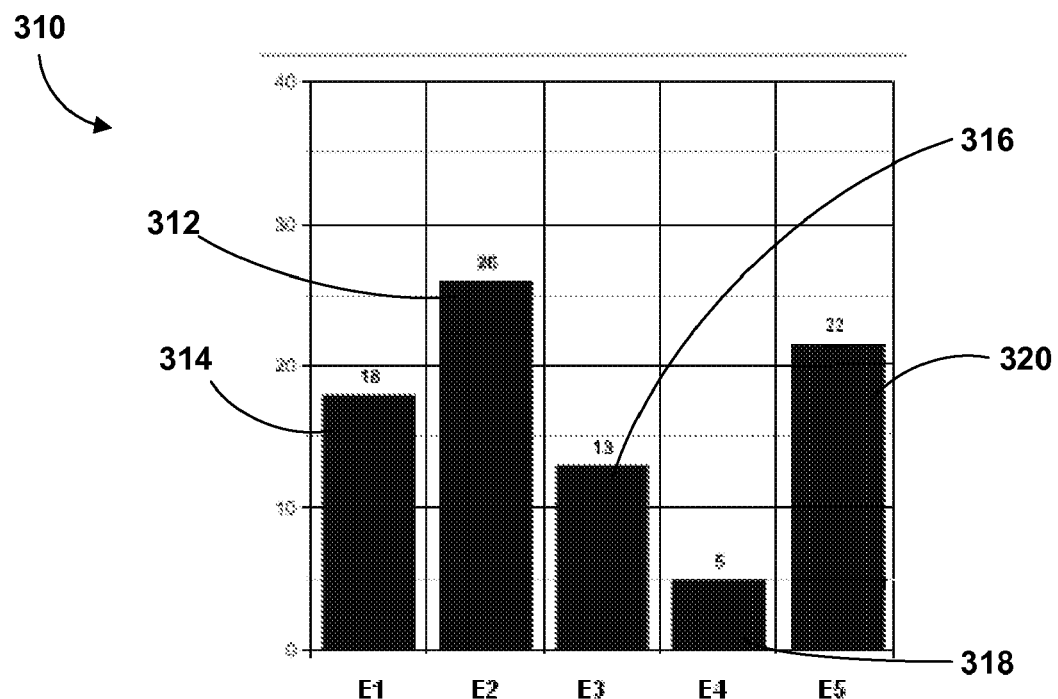

FIG. 9C illustrates an example of a bar graph 310, which includes the number of event markers on the y-axis, and the severity/efficacy rating on the x-axis. In this example the severity is ranked as E1, which indicates patient 14 did not experience a seizure, E2, which indicates patient 14 experienced a relatively minimal/non-consequential seizure, E3, which indicates patient 14 experienced a relatively minor seizure, and E4, which indicated patient 14 experienced a relatively more intense seizure than E3.

Severity/efficacy rating E5 may represent the number of times that patient 14 provided information to patient programmer 24 indicating that the activation of event indication button 58 had little to no effect on the severity of a seizure. In examples in which activating event indication button 58 results in a therapy adjustment, e.g., an adjustment of the therapy program used by IMD 16 to deliver therapy or a restarting of a therapy cycle, rating E5 may be useful for determining whether the therapy adjustment is sufficient. For example, the clinician may find that the threshold for determining whether to shift therapy programs should be lowered in order to provide more efficacious adjustment of therapy in response to activation of event indication button 58. In examples in which patient programmer 24 is operating in a placebo mode and activating event indication button 58 does not result in any therapy adjustment, but patient 14 is led to believe it results in a therapy adjustment, rating E5 may be useful for determining whether a functional event indication button 58 may be useful for patient 14.

Bar 314 represents the number of times (18) patient 14 did not experience a seizure after an event marker was generated, i.e., after activating event indication button 58. Similarly, bar 312 represents the number of times (26) patient 14 did not experience a minimal seizure after an event marker was generated. Bar 316 represents the number of times (13) patient 14 experienced a relatively minor seizure after activating event indication button 58, bar 318 represents the number of times (5) patient 14 experienced a relatively severe seizure after activating event indication button 56, and bar 320 represents the number of times (22) activating event indication button 56 did not affect the occurrence of a seizure.

Bar graphs or histograms may allow the concise and clear presentation of a variety of event information, including, for example, the number of seizures occurring in a given time period, the relatively number of different types of seizures, the number of seizures experienced in each therapy parameter set, the seizure frequency for each type for each therapy parameter set, drug concentrations for each drug administered, the severity of seizure for each of a number of activities, the duration of stimulation therapy for each of a number of drug types, the number of seizures of each type, severity, or duration, and the like. In some examples, three-dimensional bar graphs may be used to represent data on three axes. This may be desired in certain examples, such as displaying the frequency of each type of seizure for a number of therapy parameter sets. Other three-dimensional may be useful including, for example, surface maps and the like.

Just as with the other types of displays shown in FIGS. 9A and 9B, a clinician may more quickly ascertain relevant trends or relationships between the types of event information from bar graph 310 compared to a linear presentation of information (e.g., a table listing all event markers and associated event information).

Figure 9D:
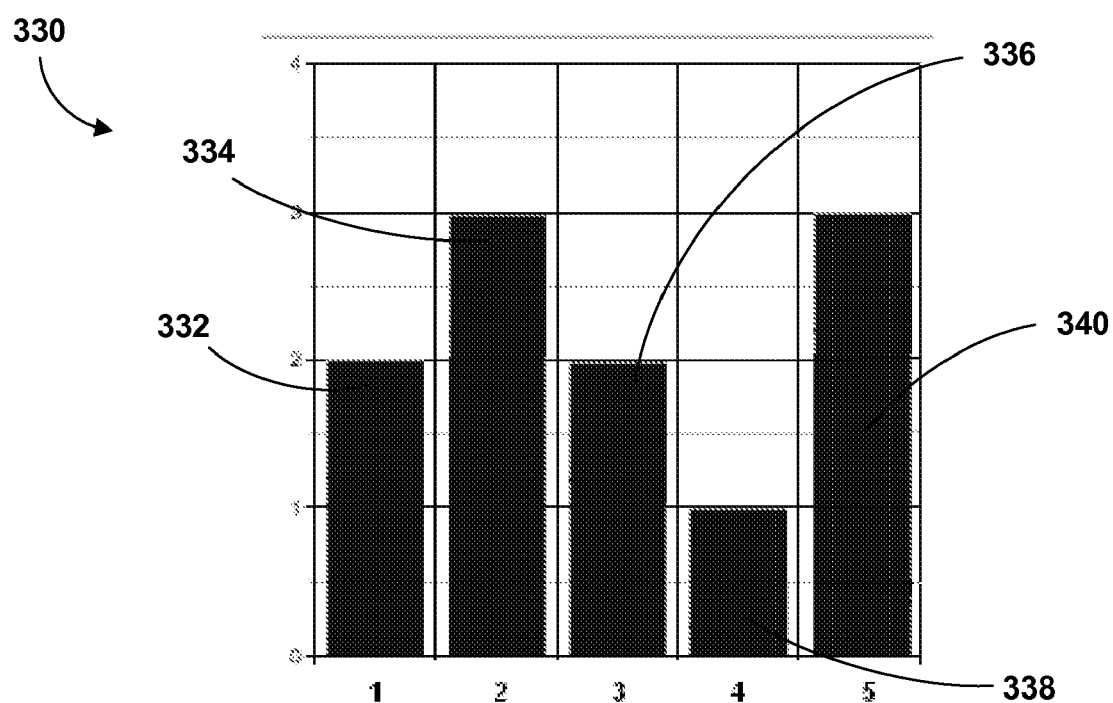

FIG. 9D illustrates an example of a histogram 330 representing of the effectiveness of therapy on the patient's condition. In the example of the histogram 330 shown in FIG. 9D, a ranking of "1" indicates little to no effect, and a ranking of "5" indicates a strong effect. For example, in the case of epilepsy, the y-axis represents the number of seizures corresponding to each ranking. Each of bars 332, 334, 336, 338, 340 represent the number of seizures that were affected by the therapy to the extent indicated by the category label.

Figure 9E:
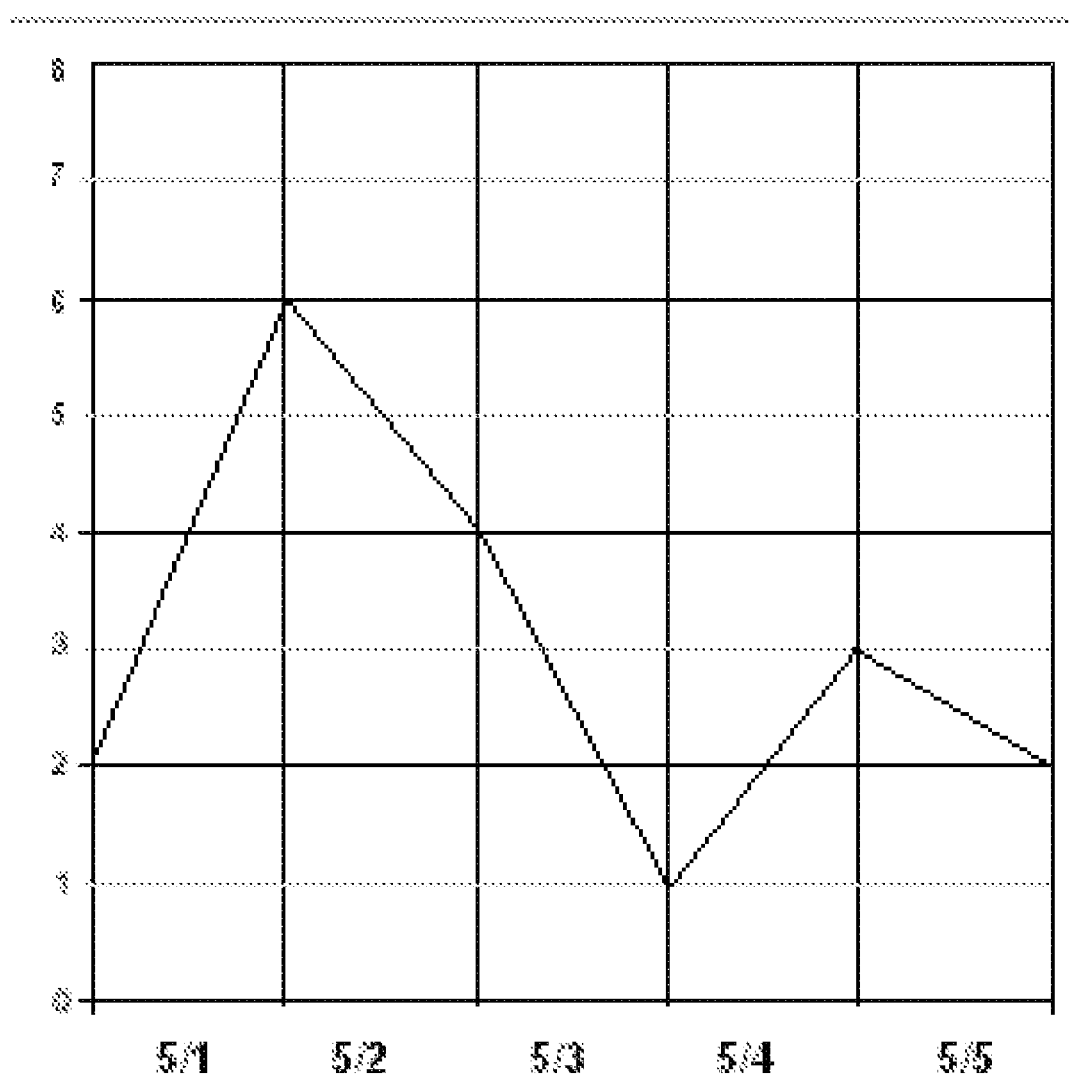

FIG. 9E illustrates an example of a line graph 350 representing the number of event markers generated per day, thereby representing the number of times patient 14 activated event indication button 58. In this example, the x-axis includes a plurality of dates. However, in other examples, the x-axis may be scaled to represent any desired time period, including, for example, a period of hours, a week, a month, and the like. Line graphs may enable a clinician to quickly ascertain any trends in the event occurrence data. Other types of event information may be represented as line graphs, including any of the event information described above. Event information that varies with time may be particularly suited for display using a line graph.

FIG. 9F illustrates a relatively large amount of event information presented in tabular format 360. Table format 360 may allow a clinician to view detailed information about a single event or a small number of events, or may allow aggregation of many events into a single grouping (e.g., a week or a month). A tabular format may be particularly useful when viewing the notes entered by patient 14 regarding the events and related therapy, and may also be preferred when viewing summary data, such as the total number of event since the last office visit, or the average number of events per time period.

In each of the examples described above, certain tasks performed by processor 40 of patient programmer 24 may be performed by a processor of another computing device, such as clinician programmer 22 or by a clinician. For example, in FIG. 5, a clinician or a processor of another computing device may associate event information with an event marker, e.g., based on the date and time the event marker was generated and the event information was received. Furthermore, each of the features described herein may be performed via hardware, software, firmware, or any combination thereof.

Various examples have been described in the disclosure. These and other examples are within the scope of the disclosure. For example, while the examples described herein are primarily directed toward therapy system 10 that includes an implanted medical device to deliver DBS, the disclosure is not so limited. In other examples, for example, therapy system 10 may include an external DBS device, an implanted or external electrical stimulator configured to deliver therapy to treat other patient conditions, a fluid delivery device configured to deliver pharmaceutical agents, insulin, pain relieving agents, gene therapy agents, or the like to patient 14, one or more microstimulators or other therapy devices.

The systems and methods described herein are also useful with therapy systems that provide an electrical stimulator, fluid (e.g., drug) delivery device or another therapy device that provides therapy to patient 14 to manage a patient condition other than a seizure disorder. For example, the systems and methods described herein are also useful with therapy systems that provide therapy for neurological disorders, psychiatric disorders, pain mitigation, peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain) or sacral nerve stimulation to influence the behavior of the relevant structures, such as the bladder, sphincter and pelvic floor muscles. For example, the systems and methods described herein may also be useful with spinal cord stimulation, gastric stimulation, pelvic floor stimulation, peripheral nerve stimulation, peripheral nerve field stimulation, and the like.

In addition, while the examples described herein are primarily directed toward receiving an indication of a patient event that is related to a seizure and receiving event information related to the seizure or seizure symptom, in other examples, a patient programmer may include an event indication button that generates a log of patient events related to other patient conditions. For example, a patient may activate the event indication button to indicate the occurrence of a headache (e.g., migraine headache, cluster headache, tension headache, cervicogenic headache or occipital neuralgia), which may be useful if the patient is afflicted with chronic pain or migraines. The patient may then provide information relating to the headache, such as the efficacy of therapy. Efficacy of therapy may include, for example, a type of headache, a severity of the headache, a duration of the headache, or a comparison of severity and/or duration of the headache to a baseline condition (e.g., a headache when therapy is not applied or a headache before a therapy system was implanted). Efficacy of therapy may also include an indication of the absence of a headache or the reduction in a severity of a headache compared to a baseline after the patient perceived an imminent headache and activated event indication button 58 of patient programmer 24.

As another example, a patient may activate event indication button 58 to indicate the occurrence of psychiatric disorder event, which may include a symptom or a mood state related to a psychiatric disorder. Psychiatric disorders may include, for example, major depressive disorder (MDD), bipolar disorder, anxiety disorders, post-traumatic stress disorder, dysthymic disorder, and obsessive-compulsive disorder (OCD). For example, as patient may activate the event indication button to indicate the occurrence of an anxiety event (e.g., an anxiety or panic attack) or the occurrence of a compulsion or obsessive thought (i.e., an obsessive-compulsive event), which may be useful if the patient is afflicted with OCD.

A patient also may activate the event indication button to indicate the occurrence of a depression event (or episode), which may be useful if the patient is afflicted with major depressive disorder, anxiety disorder, bipolar disorder, or another psychological disorder. A depression event may include a symptom of depression, such as fatigue, anhedonia, depressed mood, loss of energy, diminished ability to think or concentrate, indecisiveness, or recurrent thoughts of death or suicidal ideation, insomnia or hypersomnia. As an example, the patient symptoms may be defined by the Diagnostic and Statistical Manual of Mental Disorders (DSM-IV), which is a book, published by the American Psychiatric Association, which defines criteria used to diagnose various mental disorders, including depression.

As another example, a patient may activate the event indication button to indicate the occurrence of a manic event (or episode), which may be useful if the patient is afflicted with bipolar disorder. Examples of manic events include inflated self-esteem or grandiosity and a decreased need for sleep.

The patient may also provide information relating to the psychiatric disorder, such as the efficacy of therapy. Efficacy of therapy with respect to a psychiatric disorder may include, for example, an improvement in mood or function, an absence or reduction in severity of an anxiety attack or obsessive compulsive act after the patient perceives an imminent attack, the overall reduction in frequency of the psychiatric disorder symptom or mood state, or the like.

Patients afflicted with physical or psychological dependency (i.e., addiction), e.g., to a drug, alcohol, eating, gambling, or other activities or substances, may provide patient input to indicate the occurrence of withdrawal symptoms or cravings. The patient may also provide information relating to efficacy of therapy delivery for treating the dependency.

With respect to patients afflicted with urinary or fecal incontinence, the patient event indications may indicate the occurrence of a urinary or fecal voiding event or an urge to void felt by the patient. For example, the patient may provide input indicating the occurrence of the urinary or fecal voiding event or the voiding event may automatically be detected, e.g., with the aid of sensors. The sensors may be carried external to the patient, e.g., included within an undergarment worn by the patient as described in U.S. patent application Ser. No. 11/414,626, which was filed on Apr. 28, 2006 and is entitled, "EXTERNAL VOIDING SENSOR SYSTEM," which is incorporated herein by reference in its entirety. In other examples, the sensors may be implanted within the patient and sense physiological parameters associated with the voiding, such as electrical activity of the pelvic floor muscles, movement of fluid through the patient's body, and the like.

As another example, a patient may activate the event indication button to indicate the occurrence of a tremor episode or another symptom of a movement disorder, such as rigidity, bradykinesia, rhythmic hyperkinesia, nonrhythmic hyperkinesia, dystonia, and akinesia, which may be useful if the patient is afflicted with a movement disorder (e.g., Parkinson's disease or Huntington's disease). The patient may also provide information relating to the movement disorder, such as the efficacy of therapy. Efficacy of therapy with respect to a movement disorder may include, for example, an improvement in motion or motor function, an absence of motion reduction, or the like. Use of a patient programmer including an event indication button may also be useful with other patient events and conditions.

In each of the other examples of event indication buttons described above, patient programmer 24 may generate a signal that causes IMD 16 to adjust therapy in response to the generation of the event marker. For example, IMD 16 may change therapy programs if a certain threshold number of event markers are associated with the current therapy program, adjust a therapy parameter (e.g., increasing intensity of stimulation or a concentration or size of a drug bolus), or restart a therapy cycle.

The invention claimed is:

1. A method comprising:
   receiving, with at least one of a medical device programmer or a medical device, an indication of an occurrence of a patient event, wherein the indication of the occurrence of the patient event indicates an occurrence of a symptom of a condition of a patient;
   automatically generating, with at least one of the medical device programmer or the medical device, an event marker based on the indication of the patient event;
   receiving, with the medical device programmer, event information relating to the patient event from the patient, wherein the event information indicates an efficacy of therapy that was delivered to the patient to manage the condition of the patient prior to or during the occurrence of the patient event;
   receiving, with the medical device programmer, additional information relating to the patient event, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event;
   with at least one of the medical device programmer or the medical device, associating the event information and the additional information with the event marker; and
   with at least one of the medical device programmer or the medical device, storing the event information, the additional information, and the associated event marker within a memory.

2. The method of claim 1, wherein the patient event comprises at least one of a seizure symptom, a headache, an anxiety event, a depressive event, a manic event, an obsessive-compulsive event, a urinary or fecal incontinence event or a movement disorder symptom.

3. The method of claim 1, further comprising transmitting the event information, the additional information, and the event marker from at least one of the medical device or the medical device programmer to a computing device.

4. The method of claim 1, wherein the event information further comprises at least one of a type of the patient event, a type of drug taken prior to the occurrence of the patient event, or a drug dosage taken prior to the occurrence of the patient event.

5. The method of claim 1, wherein receiving the indication of the patient event comprises receiving the indication from the patient via the medical device programmer.

6. The method of claim 1, further comprising displaying at least one of the event information or the additional information to a user via a display device.

7. The method of claim 6, wherein the displaying the at least one of the event information or the additional information to the user comprises generating a graphical or linear display of the event information and displaying the graphical or linear display to the user via the display device.

8. The method of claim 1, wherein the event marker comprises a time and date indication.

9. The method of claim 1, wherein the additional information comprises the physiological parameter data, the method further comprising:
   with at least one of the medical device programmer or the medical device, collecting the physiological parameter data from the sensor; and
   with at least one of the medical device programmer or the medical device, associating the physiological parameter data with the event marker in the memory.

10. The method of claim 1, wherein the additional information comprises the duration of the patient event, and wherein the indication of the patient event comprises a first indication, the method further comprising:
    receiving a second indication upon completion of the patient event; and
    determining, with at least one of the medical device programmer or the medical device, the duration of the patient event based on the first indication and the second indication.

11. A system comprising:
    an event indication input mechanism;
    a user interface;
    a memory; and
    a processor configured to generate an event marker upon activation of the event indication input mechanism, the activation of the event indication input mechanism indicating an occurrence of a patient event, wherein the indication of the occurrence of the patient event indicates an occurrence of a symptom of a condition of a patient, and wherein the processor is configured to prompt the patient to input event information relating to the occurrence of the symptom, receive the event information from the patient via the user interface, and receive additional information relating to the patient event, the additional information comprising at least one of physiological parameter data collected by a sensor prior to or during the occurrence of the patient event, an identification of a type of patient event indicated by the activation of the event indication input mechanism, a duration of the patient event, a rating of a severity of the patient event, or an activity engaged in by the patient prior to the occurrence of the patient event, and wherein the processor is configured to associate the event marker with the event information and the additional information, and store the event information, the additional information, and associated event marker in the memory, and wherein the event information indicates an efficacy of therapy that was delivered to the patient to manage the patient condition prior to or during the occurrence of the patient event.

12. The system of claim 11, further comprising a telemetry module, wherein the processor is configured to transmit the event information and the additional information to a computing device via the telemetry module.

13. The system of claim 11, further comprising a display, wherein the processor is configured to prompt a user to select a type of at least one of the event information or the additional information to display and present the selected type of the at least one of the event information and the additional information via the display.

14. The system of claim 11, further comprising a display, wherein the processor is configured to present at least one of the event information or the additional information via the display as at least one of a linear display or a graphical display of the event information or the additional information.

15. The system of claim 11, further comprising a display, wherein the processor is configured to present at least one of the event information or the additional information via the display as at least one of a table, list, Venn diagram or graph of the event information or the additional information.

16. The system of claim 11, wherein the event information further comprises at least one of a type of the patient event, a type of drug taken prior to the occurrence of the patient event, or a drug dosage taken prior to the occurrence of the patient event.

17. The system of claim 11, wherein the additional information comprises the physiological parameter data, the system further comprising the sensor configured to sense a physiological parameter of the patient, wherein the processor is configured to receive the physiological parameter data from the sensor and associate the physiological parameter data with the event marker in the memory.

18. The system of claim 11, wherein the additional information comprises the duration of the patient event, and wherein the activation of the event indication input mechanism comprises a first activation of the event indication input mechanism and the processor is configured to receive a second activation of the event indication input mechanism and determine the duration of the patient event based on the first and second activations of the event indication input mechanism.

19. The system of claim 11, further comprising a medical device configured to deliver the therapy to the patient to manage the patient condition, wherein the processor is configured to control the medical device to modify the therapy based on the generation of the event marker.

20. A system comprising:
an event indication input mechanism configured to receive an indication of an occurrence of a patient event from a patient, wherein the indication of the occurrence of the patient event indicates an occurrence of a symptom of a condition of a patient;
a processor configured to generate an event marker in response to receiving the indication of the occurrence of the patient event via the event indication input mechanism;
a user input mechanism configured to receive event information relating to the patient event from the patient, wherein the event information comprises an efficacy of therapy delivered by a therapy system implemented to manage a seizure disorder of the patient prior to or during the occurrence of the patient event, wherein the processor is configured to prompt the patient to input the event information relating to the occurrence of the symptom, and wherein the processor is configured to receive additional information relating to the patient event, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event; and a memory configured to store the event marker, the additional information, and the event information.

21. The system of claim 20, wherein the event information further comprises at least one of a type of the patient event, a type of drug taken prior to the occurrence of the patient event, or a drug dosage taken prior to the occurrence of the patient event.

22. The system of claim 20, wherein the processor is configured to prompt a user to select a type of at least one of the event information or the additional information, and generate a display of the selected type of the at least one of the event information or the additional information.

23. A non-transitory computer readable medium comprising instructions that, when executed by a programmable processor, cause the programmable processor to:
receive an indication of an occurrence of a patient event, wherein the indication of the occurrence of the patient event indicates an occurrence of a symptom of a condition of a patient;
generate an event marker based on the indication of the patient event;
prompt the patient to input event information relating to the occurrence of the symptom;
receive the event information relating to the patient event from the patient, wherein the event information indicates an efficacy of therapy that was delivered to the patient to manage the condition prior to or during the occurrence of the patient event;
receive additional information relating to the patient event, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event;
associate the event information and the additional information with the event marker; and
store the event information, the additional information, and associated event marker within a memory.

24. The non-transitory computer readable medium of claim 23, wherein the additional information comprises the physiological parameter data, the computer readable medium further comprising instructions that cause the programmable processor to:
collect the physiological parameter data from a sensor; and
associate the physiological parameter data with the event marker in the memory.

25. The non-transitory computer readable medium of claim 23, wherein the additional information comprises a duration of the patient event, and wherein the indication of the occurrence of the patient event comprises a first indication, the computer readable medium further comprising instructions that cause the programmable processor to:
receive a second indication indicative of a completion of the patient event; and
determine the duration of the patient event based on the first indication and the second indication.

26. A system comprising:
means for receiving an event indication from a patient, the event indication indicating an occurrence of a patient event, wherein the indication of the occurrence of the patient event indicates an occurrence of a symptom of a patient condition;
means for generating an event marker in response to the event indication;

means for prompting the patient to input event information relating to the occurrence of the symptom;

means for receiving the event information relating to the patient event from the patient, wherein the event information indicates an efficacy of therapy that was delivered to the patient to manage the patient condition prior to or during the occurrence of the patient event;

means for receiving additional information relating to the patient event from the patient, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event; and means for storing the event marker and the event information.

27. The system of claim 26, wherein the additional information comprises the physiological parameter data, the system further comprising means for sensing a physiological parameter of the patient to generate the physiological parameter data, and means for associating the physiological parameter data with the event marker in the means for storing.

28. The method of claim 1, wherein the symptom of the condition of the patient comprises at least one of an aura, a headache, a seizure, an anxiety attack, a panic attack, a compulsion, an obsessive thought, a mood state related to a psychiatric disorder, rigidity, bradykinesia, rhythmic hyperkinesia, nonrhythmic hyperkinesia, dystonia, or akinesia.

29. The method of claim 1, wherein the condition of the patient comprises a seizure disorder, a psychiatric disorder, withdrawal from a physical or psychological dependency, urinary incontinence, fecal incontinence, chronic headaches, or a movement disorder.

30. The method of claim 1, further comprising, with the medical device programmer, prompting the patient to input the event information relating to the patient event.

31. The system of claim 11, wherein the symptom of the condition of the patient comprises at least one of an aura, a headache, a seizure, an anxiety attack, a panic attack, a compulsion, an obsessive thought, a mood state related to a psychiatric disorder, rigidity, bradykinesia, rhythmic hyperkinesia, nonrhythmic hyperkinesia, dystonia, or akinesia.

32. The system of claim 11, wherein the condition of the patient comprises a seizure disorder, a psychiatric disorder, withdrawal from a physical or psychological dependency, urinary incontinence, fecal incontinence, chronic headaches, or a movement disorder.

* * * * *